(12) United States Patent
Constantineau et al.

(10) Patent No.: US 10,828,418 B2
(45) Date of Patent: Nov. 10, 2020

(54) SLIDE-ACTIVATED ANGLED INSERTER AND CANTILEVERED BALLISTIC INSERTION FOR INTRADERMAL DRUG INFUSION

(71) Applicant: Becton, Dickinson and Company, Franklin Lakes, NJ (US)

(72) Inventors: Cole Constantineau, Cambridge, MA (US); Ryan Schoonmaker, Oceanside, CA (US); Michel Bruehwiler, Newton, MA (US); Eric Bené, Lynn, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 325 days.

(21) Appl. No.: 15/919,691

(22) Filed: Mar. 13, 2018

(65) Prior Publication Data
US 2018/0200429 A1    Jul. 19, 2018

Related U.S. Application Data

(62) Division of application No. 13/302,843, filed on Nov. 22, 2011, now Pat. No. 9,950,109.

(60) Provisional application No. 61/344,969, filed on Nov. 30, 2010, provisional application No. 61/344,968, filed on Nov. 30, 2010.

(51) Int. Cl.
*A61M 5/158*        (2006.01)
(52) U.S. Cl.
CPC ..... *A61M 5/158* (2013.01); *A61M 2005/1585* (2013.01)

(58) Field of Classification Search
CPC ..................... A61M 5/158; A61M 2005/1585
See application file for complete search history.

(56) References Cited

U.S. PATENT DOCUMENTS

| | | | |
|---|---|---|---|
| 3,857,382 A | 12/1974 | Williams, Jr. et al. |
| 3,918,355 A | 11/1975 | Weber |
| 3,963,380 A | 6/1976 | Thomas, Jr. et al. |
| 4,204,538 A | 5/1980 | Cannon |
| 4,490,141 A | 12/1984 | Lacko et al. |
| 4,685,902 A | 8/1987 | Edwards et al. |
| 4,723,947 A | 2/1988 | Konopka |
| 4,734,092 A | 3/1988 | Millerd |
| 4,755,173 A | 7/1988 | Konopka et al. |
| 5,176,662 A | 1/1993 | Bartholomew et al. |
| 5,226,899 A | 7/1993 | Lee et al. |
| 5,242,406 A | 9/1993 | Gross et al. |

(Continued)

FOREIGN PATENT DOCUMENTS

| | | |
|---|---|---|
| EP | 0 980 687 | 2/2000 |
| EP | 1475113 A1 | 11/2004 |

(Continued)

*Primary Examiner* — Matthew F Desanto
(74) *Attorney, Agent, or Firm* — Dickinson Wright PLLC

(57) ABSTRACT

An infusion set configured to be secured to a skin surface for targeting a desired depth to deliver content to an upper skin surface, comprising a hub and a needle configured to travel during insertion as urged by a motion, wherein said needle is configured to assume a first angle relative to said skin surface in a free state, and wherein said needle is configured to return toward said first angle relative to said skin surface upon release of said motion, wherein said motion is at an angle relative to said skin surface that is different from said first angle of said needle.

16 Claims, 14 Drawing Sheets

(56) References Cited

U.S. PATENT DOCUMENTS

| | | |
|---|---|---|
| 5,257,980 A | 11/1993 | Van Antwerp et al. |
| 5,453,099 A | 9/1995 | Lee et al. |
| 5,522,803 A | 6/1996 | Teissen-Simony |
| 5,536,249 A | 7/1996 | Castellano et al. |
| 5,545,143 A | 8/1996 | Fischell |
| 5,545,152 A | 8/1996 | Funderburk et al. |
| 5,593,390 A | 1/1997 | Castellano et al. |
| 5,728,074 A | 3/1998 | Castellano et al. |
| 5,800,420 A | 9/1998 | Gross et al. |
| 5,820,602 A | 10/1998 | Kovelman et al. |
| 5,851,197 A | 12/1998 | Marano et al. |
| 5,858,001 A | 1/1999 | Tsals et al. |
| 5,858,005 A | 1/1999 | Kriesel |
| 5,925,021 A | 7/1999 | Castellano et al. |
| 5,957,895 A | 9/1999 | Sage et al. |
| 5,968,011 A | 10/1999 | Larsen et al. |
| 5,980,506 A | 11/1999 | Mathiasen |
| 6,017,328 A | 1/2000 | Fischell et al. |
| 6,056,718 A | 5/2000 | Funderburk et al. |
| 6,068,615 A | 5/2000 | Brown et al. |
| 6,074,369 A | 6/2000 | Sage et al. |
| 6,086,575 A | 7/2000 | Mejslov |
| 6,093,172 A | 7/2000 | Funderburk et al. |
| 6,110,148 A | 8/2000 | Brown et al. |
| 6,123,690 A | 9/2000 | Mejslov |
| 6,132,400 A | 10/2000 | Waldenburg |
| 6,175,752 B1 | 1/2001 | Say et al. |
| 6,206,134 B1 | 3/2001 | Stark et al. |
| 6,254,586 B1 | 7/2001 | Mann et al. |
| 6,272,364 B1 | 8/2001 | Kurnik |
| 6,275,717 B1 | 8/2001 | Gross et al. |
| 6,277,627 B1 | 8/2001 | Hellinga |
| 6,293,925 B1 | 9/2001 | Safabash et al. |
| 6,302,866 B1 | 10/2001 | Marggi |
| 6,352,523 B1 | 3/2002 | Brown et al. |
| 6,355,021 B1 | 3/2002 | Nielsen et al. |
| 6,391,005 B1 | 5/2002 | Lum et al. |
| 6,485,461 B1 | 11/2002 | Mason et al. |
| 6,520,938 B1 | 2/2003 | Funderburk et al. |
| 6,521,446 B2 | 2/2003 | Hellinga |
| 6,544,212 B2 | 4/2003 | Galley et al. |
| 6,546,269 B1 | 4/2003 | Kurnik |
| 6,551,276 B1 | 4/2003 | Mann et al. |
| 6,558,351 B1 | 5/2003 | Steil et al. |
| 6,565,509 B1 | 5/2003 | Say et al. |
| 6,576,430 B1 | 6/2003 | Hsieh et al. |
| 6,579,267 B2 | 6/2003 | Lynch et al. |
| 6,589,229 B1 | 7/2003 | Connelly et al. |
| 6,607,509 B2 | 8/2003 | Bobroff et al. |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,692,457 B2 | 2/2004 | Flaherty |
| 6,699,218 B2 | 3/2004 | Flaherty et al. |
| 6,706,159 B2 | 3/2004 | Moerman et al. |
| 6,723,072 B2 | 4/2004 | Flaherty et al. |
| 6,740,059 B2 | 5/2004 | Flaherty |
| 6,749,560 B1 | 6/2004 | Konstrorum et al. |
| 6,749,587 B2 | 6/2004 | Flaherty |
| 6,768,425 B2 | 7/2004 | Flaherty et al. |
| 6,830,558 B2 | 12/2004 | Flaherty et al. |
| 6,830,562 B2 | 12/2004 | Mogensen et al. |
| 6,840,922 B2 | 1/2005 | Nielsen et al. |
| 6,852,104 B2 | 2/2005 | Blomquist |
| 6,949,084 B2 | 9/2005 | Marggi et al. |
| 6,960,162 B2 | 11/2005 | Saadat et al. |
| 6,960,192 B1 | 11/2005 | Flaherty et al. |
| 6,977,180 B2 | 12/2005 | Hellinga et al. |
| 6,997,907 B2 | 2/2006 | Safabash et al. |
| 7,004,928 B2 | 2/2006 | Aceti et al. |
| 7,018,360 B2 | 3/2006 | Flaherty et al. |
| 7,029,455 B2 | 4/2006 | Flaherty |
| 7,052,251 B2 | 5/2006 | Nason et al. |
| 7,052,483 B2 | 5/2006 | Wojcik |
| 7,064,103 B2 | 6/2006 | Pitner et al. |
| 7,070,580 B2 | 7/2006 | Nielsen |
| 7,083,597 B2 | 8/2006 | Lynch et al. |
| 7,109,878 B2 | 9/2006 | Mann et al. |
| 7,128,727 B2 | 10/2006 | Flaherty et al. |
| 7,137,964 B2 | 11/2006 | Flaherty |
| 7,144,384 B2 | 12/2006 | Gorman et al. |
| 7,207,974 B2 | 4/2007 | Safabash et al. |
| 7,214,207 B2 | 5/2007 | Lynch et al. |
| 7,226,278 B2 | 6/2007 | Nason et al. |
| 7,303,543 B1 | 12/2007 | Maule et al. |
| 7,303,549 B2 | 12/2007 | Flaherty et al. |
| 7,310,544 B2 | 12/2007 | Brister et al. |
| 7,318,816 B2 | 1/2008 | Bobroff et al. |
| 7,329,239 B2 | 2/2008 | Safabash et al. |
| 7,354,420 B2 | 4/2008 | Steil et al. |
| 7,496,392 B2 | 2/2009 | Alarcon et al. |
| 7,713,258 B2 | 5/2010 | Adams et al. |
| 7,722,595 B2 | 5/2010 | Pettis et al. |
| 8,083,715 B2 | 12/2011 | Sonoda et al. |
| 8,172,803 B2 | 5/2012 | Morrissey et al. |
| 8,221,359 B2 | 7/2012 | Kristensen et al. |
| 8,262,618 B2 | 9/2012 | Scheurer |
| 8,277,415 B2 | 10/2012 | Mounce et al. |
| 8,285,328 B2 | 10/2012 | Caffey et al. |
| 8,287,467 B2 | 10/2012 | List et al. |
| 8,287,516 B2 | 10/2012 | Kornerup et al. |
| 8,306,596 B2 | 11/2012 | Schurman et al. |
| 8,310,415 B2 | 11/2012 | McLaughlin et al. |
| 8,313,468 B2 | 11/2012 | Geipel et al. |
| 9,174,006 B2* | 11/2015 | Vosseler .............. A61M 5/3293 |
| 9,950,109 B2* | 4/2018 | Constantineau ...... A61M 5/158 |
| 2002/0040208 A1 | 4/2002 | Flaherty et al. |
| 2003/0055380 A1 | 3/2003 | Flaherty |
| 2003/0109829 A1 | 6/2003 | Mogensen et al. |
| 2003/0176852 A1 | 9/2003 | Lynch et al. |
| 2003/0199823 A1 | 10/2003 | Bobroff et al. |
| 2004/0002682 A1 | 1/2004 | Kovelman et al. |
| 2004/0010207 A1 | 1/2004 | Flaherty et al. |
| 2004/0044306 A1 | 3/2004 | Lynch et al. |
| 2004/0059316 A1 | 3/2004 | Smedegaard |
| 2004/0078028 A1 | 4/2004 | Flaherty et al. |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0162521 A1 | 8/2004 | Bengtsson |
| 2004/0204673 A1 | 10/2004 | Flaherty |
| 2004/0204687 A1 | 10/2004 | Mogensen et al. |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0043687 A1 | 2/2005 | Mogensen et al. |
| 2005/0065760 A1 | 3/2005 | Murtfeldt et al. |
| 2005/0090784 A1 | 4/2005 | Nielsen et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0113761 A1 | 5/2005 | Faust et al. |
| 2005/0124936 A1 | 6/2005 | Mogensen et al. |
| 2005/0171512 A1 | 8/2005 | Flaherty |
| 2005/0182366 A1 | 8/2005 | Vogt et al. |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | Dilanni et al. |
| 2005/0245799 A1 | 11/2005 | Brauker et al. |
| 2005/0273076 A1 | 12/2005 | Beasley et al. |
| 2005/0283144 A1 | 12/2005 | Shiono et al. |
| 2006/0001551 A1 | 1/2006 | Kraft et al. |
| 2006/0041229 A1 | 2/2006 | Garibotto et al. |
| 2006/0074381 A1 | 4/2006 | Malave et al. |
| 2006/0122577 A1 | 6/2006 | Poulsen et al. |
| 2006/0129090 A1 | 6/2006 | Moberg et al. |
| 2006/0135913 A1 | 6/2006 | Ethelfeld |
| 2006/0142698 A1 | 6/2006 | Ethelfeld |
| 2006/0173410 A1 | 8/2006 | Moberg et al. |

(56) References Cited

U.S. PATENT DOCUMENTS

| | | |
|---|---|---|
| 2006/0178633 A1 | 8/2006 | Garibotto et al. |
| 2006/0200073 A1 | 9/2006 | Radmer et al. |
| 2006/0263839 A1 | 11/2006 | Ward et al. |
| 2006/0264835 A1 | 11/2006 | Nielsen et al. |
| 2006/0282290 A1 | 12/2006 | Flaherty et al. |
| 2007/0016149 A1 | 1/2007 | Hunn et al. |
| 2007/0021733 A1 | 1/2007 | Hansen et al. |
| 2007/0049865 A1 | 3/2007 | Radmer et al. |
| 2007/0073229 A1 | 3/2007 | Gorman et al. |
| 2007/0073559 A1 | 3/2007 | Stangel |
| 2007/0088244 A1 | 4/2007 | Miller et al. |
| 2007/0088271 A1 | 4/2007 | Richards |
| 2007/0093754 A1 | 4/2007 | Mogensen et al. |
| 2007/0118405 A1 | 5/2007 | Campbell et al. |
| 2007/0149925 A1 | 6/2007 | Edwards et al. |
| 2007/0191702 A1 | 8/2007 | Yodfat et al. |
| 2007/0219496 A1 | 9/2007 | Kamen et al. |
| 2008/0004515 A1 | 1/2008 | Jennewine |
| 2008/0021395 A1 | 1/2008 | Yodfat et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051730 A1 | 2/2008 | Bikovsky |
| 2008/0051738 A1 | 2/2008 | Griffin |
| 2008/0051765 A1 | 2/2008 | Mounce |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0103483 A1 | 5/2008 | Johnson et al. |
| 2008/0116647 A1 | 5/2008 | Anderson et al. |
| 2008/0119707 A1 | 5/2008 | Stafford |
| 2008/0132842 A1 | 6/2008 | Flaherty |
| 2008/0147041 A1 | 6/2008 | Kristensen |
| 2008/0160492 A1 | 7/2008 | Campbell et al. |
| 2008/0194924 A1 | 8/2008 | Valk et al. |
| 2008/0204077 A1 | 8/2008 | Huang |
| 2008/0215006 A1 | 9/2008 | Thorkild |
| 2008/0228144 A1 | 9/2008 | Liniger et al. |
| 2008/0261255 A1 | 10/2008 | Tolosa et al. |
| 2008/0264261 A1 | 10/2008 | Kavazov et al. |
| 2008/0269680 A1 | 10/2008 | Ibranyan et al. |
| 2008/0269687 A1 | 10/2008 | Chong et al. |
| 2008/0269713 A1 | 10/2008 | Kavazov |
| 2008/0281297 A1 | 11/2008 | Pesach et al. |
| 2008/0294028 A1 | 11/2008 | Brown |
| 2008/0306434 A1 | 12/2008 | Dobbles et al. |
| 2008/0312608 A1 | 12/2008 | Christoffersen et al. |
| 2008/0319414 A1 | 12/2008 | Yodfat et al. |
| 2009/0005724 A1 | 1/2009 | Regittnig et al. |
| 2009/0005728 A1 | 1/2009 | Weinert et al. |
| 2009/0012472 A1 | 1/2009 | Ahm et al. |
| 2009/0062767 A1 | 3/2009 | Van Antwerp et al. |
| 2009/0076453 A1 | 3/2009 | Mejlhede et al. |
| 2009/0198191 A1 | 8/2009 | Chong et al. |
| 2009/0198215 A1 | 8/2009 | Chong et al. |
| 2009/0221971 A1 | 9/2009 | Mejlhede et al. |
| 2009/0240240 A1 | 9/2009 | Hines et al. |
| 2009/0254041 A1 | 10/2009 | Krag et al. |
| 2009/0281497 A1 | 11/2009 | Kamen et al. |
| 2009/0326457 A1 | 12/2009 | O'Connor |
| 2010/0049129 A1 | 2/2010 | Yokoi et al. |
| 2010/0160902 A1 | 6/2010 | Aeschilimann et al. |
| 2010/0204652 A1 | 8/2010 | Morrissey et al. |
| 2010/0222743 A1 | 9/2010 | Frederickson et al. |
| 2010/0286714 A1 | 11/2010 | Gyrn et al. |
| 2010/0291588 A1 | 11/2010 | McDevitt et al. |
| 2010/0298830 A1 | 11/2010 | Browne et al. |
| 2011/0046456 A1* | 2/2011 | Hordum ............ A61M 5/14248 600/309 |
| 2012/0253282 A1 | 10/2012 | Nagel et al. |
| 2012/0259185 A1 | 10/2012 | Yodfat et al. |
| 2012/0265034 A1 | 10/2012 | Wisniewski et al. |
| 2012/0277554 A1 | 11/2012 | Schurman et al. |
| 2012/0277667 A1 | 11/2012 | Yodat et al. |
| 2012/0277724 A1 | 11/2012 | Larsen et al. |
| 2012/0283540 A1 | 11/2012 | Brüggemann |
| 2012/0291778 A1 | 11/2012 | Nagel et al. |
| 2012/0293328 A1 | 11/2012 | Blomquist |
| 2012/0296269 A1 | 11/2012 | Blomquist |
| 2012/0296310 A1 | 11/2012 | Blomquist |
| 2012/0296311 A1 | 11/2012 | Brauker et al. |

FOREIGN PATENT DOCUMENTS

| | | |
|---|---|---|
| EP | 1475113 A1 | 11/2004 |
| EP | 1 698 279 A1 | 9/2006 |
| EP | 1698279 A1 | 9/2006 |
| JP | 2003520082 | 1/2000 |
| JP | 200352672 | 2/2003 |
| WO | WO-95/10313 A1 | 4/1995 |
| WO | WO 99-34212 | 7/1999 |
| WO | WO 2007-051139 | 5/2007 |
| WO | WO 2007052662 | 5/2007 |
| WO | WO 2007/140632 A1 | 12/2007 |
| WO | WO 2 445 437 A | 7/2008 |
| WO | WO 2009-021039 | 2/2009 |
| WO | WO 2009-021052 | 2/2009 |
| WO | WO 2009/103759 A1 | 8/2009 |

* cited by examiner

SLIDE-ACTIVATED ANGLED INSERTER AND CANTILEVERED BALLISTIC INSERTION FOR INTRADERMAL DRUG INFUSION

CROSS-REFERENCE TO RELATED APPLICATIONS

This application is a division of U.S. patent application Ser. No. 13/302,843, filed on Nov. 22, 2011, which claims the benefit under 35 U.S.C. § 119(e) of U.S. Provisional Application Ser. No. 61/344,968, filed on Nov. 30, 2010, and U.S. Provisional Application Ser. No. 61/344,969, filed on Nov. 30, 2010, the entire content of each of said applications being incorporated herein by reference.

FIELD OF THE INVENTION

The present invention relates generally to intradermal infusion sets, including an adhesive secured main hub, and a slidable top cover, needle hub and angled or cantilevered needle, that can be used for performing an intradermal needle insertion precisely targeting the upper 3 mm of skin surface, for example, one that substantially duplicates the Mantoux insertion technique, for injecting into the intradermal layer of skin.

BACKGROUND OF THE INVENTION

A large number of people, including those suffering from conditions such as diabetes use some form of infusion therapy, such as daily insulin infusions to maintain close control of their glucose levels. There are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness.

The use of an infusion pump requires the use of a disposable component, typically referred to as an infusion set or pump set, which conveys the insulin from a reservoir within the pump into the skin of the user. An infusion set typically consists of a pump connector, a length of tubing, and a hub or base from which an infusion needle or cannula extends. The hub or base has an adhesive which retains the base on the skin surface during use, which may be applied to the skin manually or with the aid of a manual or automatic insertion device.

Currently, most insulin infusion sets deliver insulin to the sub-cutaneous layers of skin using either fixed metal needles or flexible plastic cannulas. Such infusion sets typically deliver insulin 4-10 mm below the skin surface. However, the upper 3 mm of skin surface, the intradermal space, facilitates better drug absorption. Unfortunately, due to the relative thinness of the intradermal layer, inserting a needle at such depth and maintaining an infusion site over an extended period of time within this narrow band is difficult.

One technique to provide intradermal injection is the Mantoux technique. As known to those skilled in the art, the Mantoux technique is typically used when administering tuberculosis tests. Skilled nurses first stretch taut the selected area of skin between the thumb and forefinger, and then insert the needle slowly, bevel upward, at an angle of 5 to 15 degrees to the skin surface. The nurse then advances the needle through the epidermis approximately 3 mm, releases the stretched skin, and injects the medicament. However, even where intradermal delivery can be accomplished with the standard Mantoux technique, this method is highly variable and subject to user error.

Further, most insulin infusion sets typically do not provide any features to isolate the inserted needle from shock or other external forces. Since these infusion sets typically deliver insulin 4-10 mm below the skin surface, shock or other external forces to the set have less effect on the deeper inserted needle. However, where an attempt is made to target the upper 3 mm of skin surface, any shock or movement of the set can adversely affect needle insertion and infusion performance.

Still further, most insulin sets have inserters that can result in skin surface "tenting" during needle insertion, where the skin surface is deflected somewhat prior to or during needle insertion which makes precisely targeting the upper 3 mm of skin surface difficult.

Accordingly, a need exists for an infusion set that can deliver content to the upper 3 mm of skin surface, the intradermal space, to facilitate better drug absorption, while maintaining a degree of comfort to the user.

SUMMARY OF THE INVENTION

An object of the present invention is to provide an infusion set which can deliver insulin or other medicament to the upper 3 mm of skin surface, the intradermal space, to facilitate better drug absorption, while maintaining a degree of comfort to the user.

Another object of the present invention is to provide an infusion set that can insert a needle at an angle relative to a skin surface via a user motion, the angle of user motion being different from the angle of the inserted needle, to target and deliver insulin or other medicament to the upper 3 mm of skin surface.

Another object of the present invention is to provide an infusion set that can insert a needle at an angle to duplicate the Mantoux insertion technique and deliver insulin or other medicament to the upper 3 mm of skin surface.

Another object of the present invention is to provide an infusion set that can insert a needle using a needle-driving cantilever beam and deliver insulin or other medicament to the upper 3 mm of skin surface.

Another object of the present invention is to provide an infusion set that can insert a needle while substantially reducing tenting of the skin surface and/or precisely target the intradermal depth, and deliver insulin or other medicament to the upper 3 mm of skin surface.

Another object of the present invention is to provide an infusion set having a skin securing, adhesive layer to secure the skin surface at the insertion site such that the set can insert a needle with a reduced risk of tenting of the skin surface and/or precisely target the intradermal depth.

Another object of the present invention is to provide an infusion set having a skin securing, adhesive layer and one or more flexible elements to secure, and stretch and/or flatten the skin surface, or otherwise create skin tension, at the insertion site such that the set can insert a needle with a reduced risk of tenting of the skin surface and/or precisely target the intradermal depth.

Another object of the present invention is to provide an infusion set having one or more flexible elements to secure the inserted needle at the intradermal depth.

Another object of the present invention is to provide an exemplary infusion set including a removable top cover that can be pulled in a first direction to insert a needle in the intradermal space at an angle to duplicate the Mantoux insertion technique and deliver insulin or other medicament to the upper 3 mm of skin surface.

Another object of the present invention is to provide an infusion set including a removable top cover that can be pulled in a first direction to load a needle-driving cantilever beam and that can be pulled in a second direction to then release the needle-driving cantilever beam, insert a needle in the intradermal space and deliver insulin or other medicament to the upper 3 mm of skin surface.

Another object of the present invention is to provide an infusion set that can isolate an inserted needle from external forces such that the needle can be maintained at a depth to deliver insulin or other medicament to the upper 3 mm of skin surface during normal use.

Another object of the present invention is to provide an infusion set including an isolated needle hub to isolate an inserted needle from external forces.

Another object of the present invention is to provide an infusion set including tortuous path adhesive segment to isolate an inserted needle from external forces.

Another object of the present invention is to provide an infusion set including flexible tube segment to isolate an inserted needle from external forces.

Another object of the present invention is to provide an infusion set including a covering element to isolate an inserted needle from external forces.

These and other objects are substantially achieved by providing an infusion set having an adhesive secured main hub, and a slidable top cover, needle hub and angled needle that can be used for performing an intradermal needle insertion that substantially duplicates the Mantoux insertion technique, for injecting insulin or other medicament into the intradermal layer of skin. The infusion set can provide the sliding needle hub and angled needle, and one or more adhesive covered flexible arms to stretch and/or flatten the skin surface, or otherwise create skin tension, at the injection site to duplicate a Mantoux technique needle insertion. Position of the inserted needle can be maintained by retracting the flexible arms to hold the inserted needle in position and prevent the slidable needle hub and angled needle from retraction once in position. The main hub can be separated from at least a valve hub of the infusion set using one or more of a tortuous path adhesive segment, a flexible tube segment, and cover to isolate the inserted needle from external forces, such that the needle can be maintained at a depth to deliver insulin or other medicament to the upper 3 mm of skin surface during normal use.

These and other objects are also substantially achieved by providing an infusion set having a removable top cover to load and then release a needle-driving cantilever beam, and an isolated needle hub, to ensure proper insertion and maintenance of the inserted needle to a depth to deliver insulin or other medicament to the upper 3 mm of skin surface. Position of the inserted needle can be maintained by providing a preload to the cantilever beam and isolating the needle from external forces using one or more of a tortuous path adhesive segment, a flexible tube segment, and cover such that the needle can be maintained at a depth to deliver insulin or other medicament to the upper 3 mm of skin surface during normal use.

BRIEF DESCRIPTION OF THE DRAWINGS

The various objects, advantages and novel features of the exemplary embodiments of the present invention will be more readily appreciated from the following detailed description when read in conjunction with the appended drawings, in which.

Throughout the drawings, like reference numerals will be understood to refer to like parts, components and structures.

DETAILED DESCRIPTION OF THE EXEMPLARY EMBODIMENTS

Figure 14:
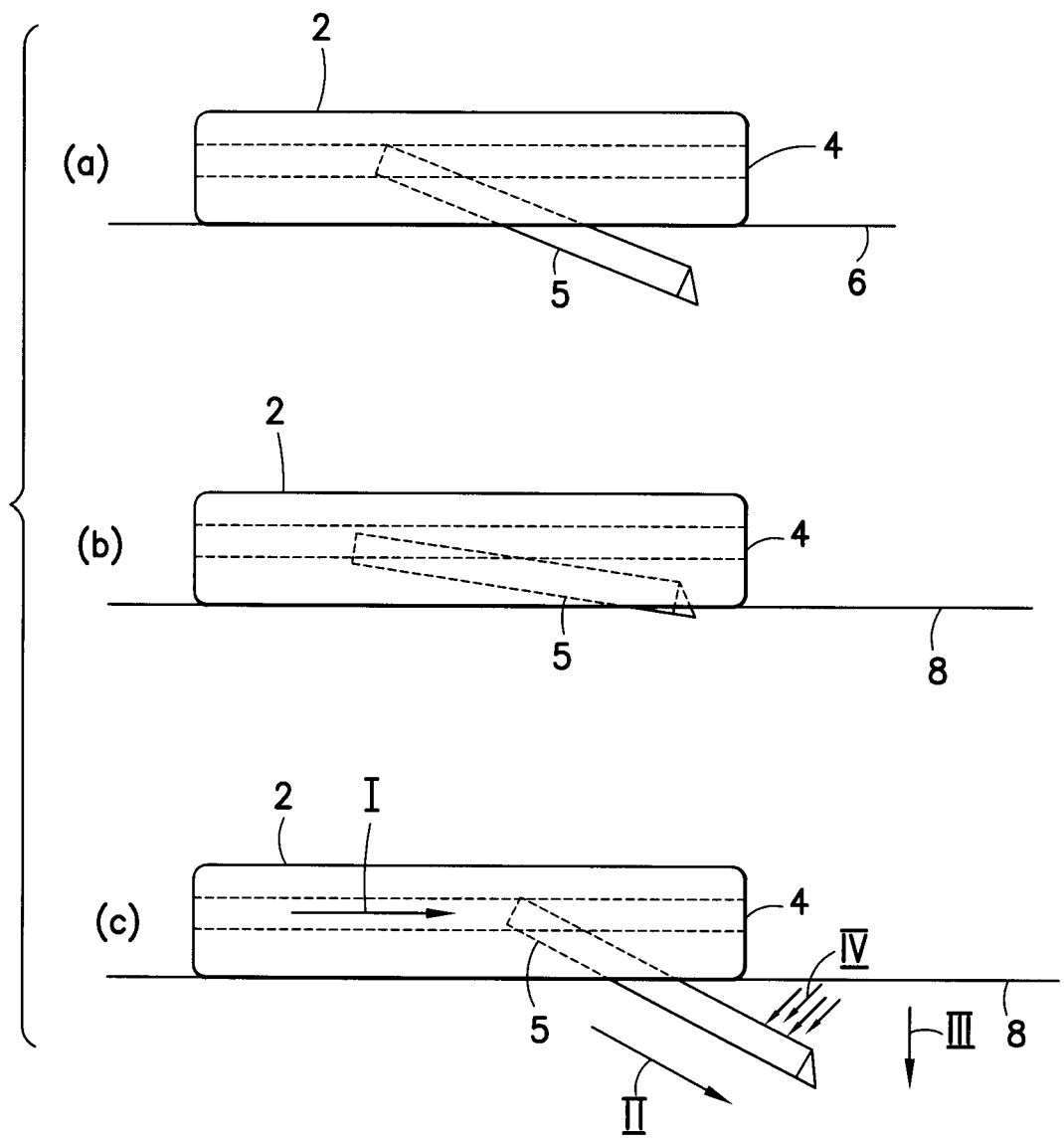
FIG. 14 is a view of an illustrative infusion set and motion that can insert a needle at an angle relative to a skin surface via a user motion, the angle of user motion being different from the angle of the inserted needle, in accordance with an embodiment of the present invention.

The exemplary embodiments of the present invention described below provide a novel means of performing an intradermal needle insertion at an angle relative to a skin surface via a user motion, the angle of user motion being different than the angle of the inserted needle. Such insertion can precisely target the upper 3 mm of skin surface and can substantially duplicate the Mantoux insertion technique, and can deliver insulin to the intradermal layers of skin via a standard insulin pump. For example, FIG. 14 is a view of an illustrative infusion set and motion that can be used to insert a needle via a user motion at an angle relative to the skin surface that is different from the angle of the inserted needle in accordance with an embodiment of the present invention. View (a) illustrates an infusion device in a free state before use, view (b) illustrates the same device once secured to a skin surface, and view (c) illustrates the same device during insertion into the skin surface at an angle relative to a skin surface via a user motion occurring at an angle to the skin surface that is different from the angle of the inserted needle, in accordance with an embodiment of the present invention.

In view (a) of FIG. 14, a hub 2 includes an insertion track 4 along which the base of the needle 5 is configured to travel during insertion as urged by a user motion. In the free state in view (a), needle 5 is at a first angle relative to a base of the hub 2, which is configured to be secured with a skin surface 8 via an adhesive layer 6. When applied to the skin surface as in view (b), the needle 5 is first deflected by the contact with the skin surface 8 toward the base of the hub 2 to a second angle, and the skin surface can tent downward by varying degrees. Thereafter, when a user motion is applied in a direction of arrow I and the needle 5 travels along track 4 at a third angle, the skin exerts an opposing force in a direction of arrows IV on the needle 5 resulting in both axial and radial motion of the needle 5 to achieve the target depth and final insertion angle. For example, when the user motion is applied, the skin force in the direction of arrows IV on the needle 5 results in axial motion in the direction of arrow II and radial motion in the direction of arrow III. Once the user motion of arrow I is removed, the forces substantially relax, resulting in a final needle insertion angle closer to that shown in view (a). The final insertion angle can be the same as or different than the first, for example, the first angle may actually start at 10 degrees relative to the base of the hub 2 and increase to 20 degrees relative to the base of the hub 2 after insertion. The needle deflection and relaxation that occur before the needle reaches its final position are believed to create a pocket in the intradermal layer of the skin that improves the intradermal delivery of insulin and other medicaments. As illustrated in FIG. 14 and implemented in exemplary embodiments of the present invention described below, the needle can be inserted at an angle relative to a skin surface via a user motion (e.g., arrow I), the angle of user motion being different from the angle of the inserted needle.

To do so, the exemplary embodiments comprise an adhesive secured main hub, and a slidable top cover, needle hub and angled or cantilevered needle that can be used for performing an intradermal needle insertion precisely targeting the upper 3 mm of skin surface, for example, one that substantially duplicates the Mantoux insertion technique. The device can be adhesively attached to a skin surface, and a slidable top cover can be used to slide an angled needle into a desired insertion position or release a cantilevered needle. Position of the inserted needle can be maintained by providing flexible arms to hold the inserted needle in position and prevent the slidable needle hub and angled needle from retraction once in position, and separation of a main hub from the valve hub of the infusion set using one or more of a tortuous path adhesive segment, a flexible tube segment, and cover can isolate the inserted needle from external forces.

The exemplary embodiments are configured to be efficient and user friendly, and the infusion set is inserted differently from typical infusion sets currently available. For example, in a first exemplary embodiment a user first peels off an adhesive backing, revealing the skin adhesive on a patient contact surface of the infusion set. Next, the device is adhered to the infusion site with a downward pressure or application force by the user. In this position, the user can now slide the top cover off the now stationary main hub and lower hub to be discarded. The sliding action of the top cover further inserts the angled needle as described in greater detail below, into the upper 3 mm of skin surface, the intradermal space, to facilitate better drug absorption. With the top cover removed, the main valve of a valve hub is revealed, and the user can then connect the insulin pump to the valve hub and commence priming of the infusion set. After such priming, standard delivery of insulin to the infusion set is provided.

Within such an exemplary infusion set, a main hub is provided which comprises a slidable, angled needle contained within an outer housing. To relieve strain, movement and vibration, the main hub is connected to the valve hub via at least one of a flexible tube, and a flexible portion or tortuous path of adhesive. The main hub provides the fluid interface to the flexible tube going to the valve hub, a solid fixation for the needle, and interfaces which bend the flexible arms on the outer housing.

To duplicate the skin tensioning, stretching and/or flattening of the Mantoux technique, the outer housing contains two flexible arms adjacent to the injection site, each provided with adhesive pads. The cover can comprise a drag arm that is configured to reach into the outer housing via a slot. When the device is pressed onto the skin surface, the flexible arms stick to the skin at the injection site. As the user pulls the top cover off the device, at least one drag arm provided by the top cover pulls the needle hub in a direction parallel to the skin surface, causing the flexible arms to move outward when contacted by the moving needle hub, thus tensioning, stretching and/or flattening the skin in preparation for needle insertion. When these flexible arms reach their maximum displacement, the angled needle moving with the needle hub penetrates the intradermal layer.

As the needle and needle hub are pulled to the end-stop contained within the outer housing, the flexible arms retract behind the needle and needle hub, creating a passive snap which holds the inserted needle in place and prevents reverse motion of the needle and needle hub. With the needle properly inserted and the top cover now removed in the same single motion, the user then attaches the pump interface to the valve hub using, for example, flexible plastic snaps. The pump interface valve is configured to allow rotation, which helps in tubing placement.

Figure 1:
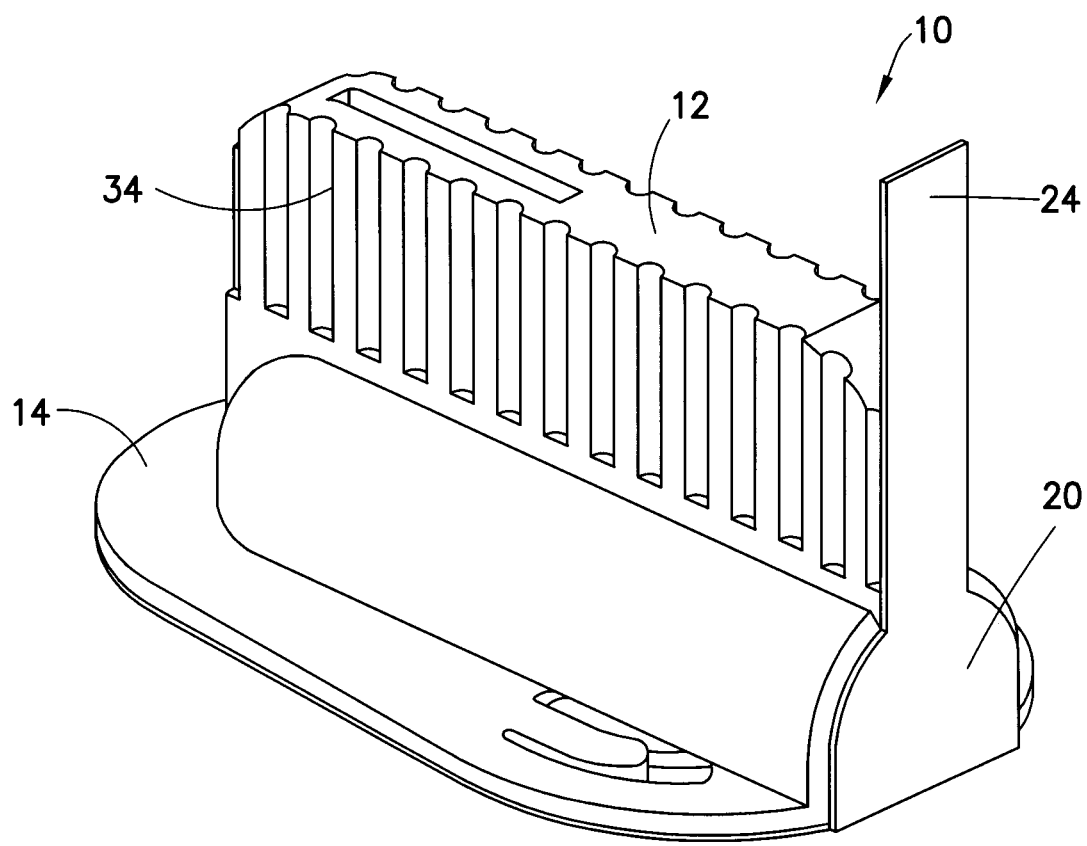
FIG. 1 is a top perspective view of an infusion set in an assembled position in accordance with an embodiment of the present invention.
Figure 2:
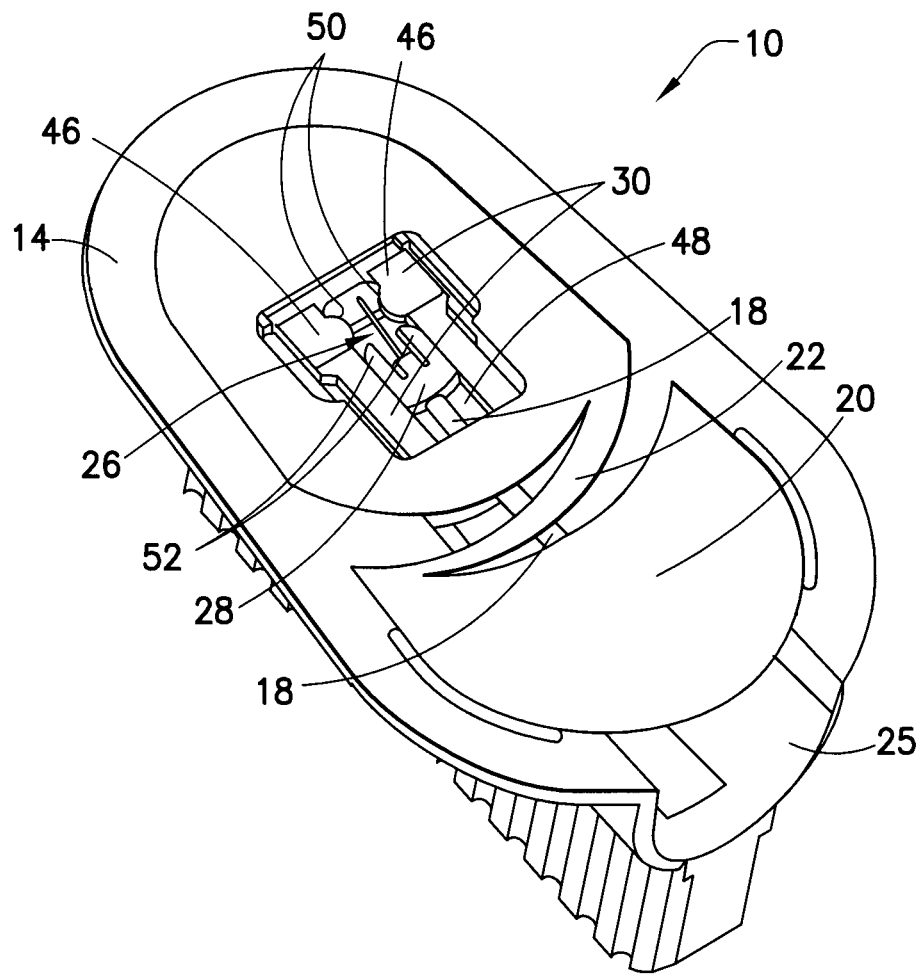
FIG. 2 is a bottom perspective view of the infusion set of FIG. 1 in accordance with an embodiment of the present invention.
Figure 3:
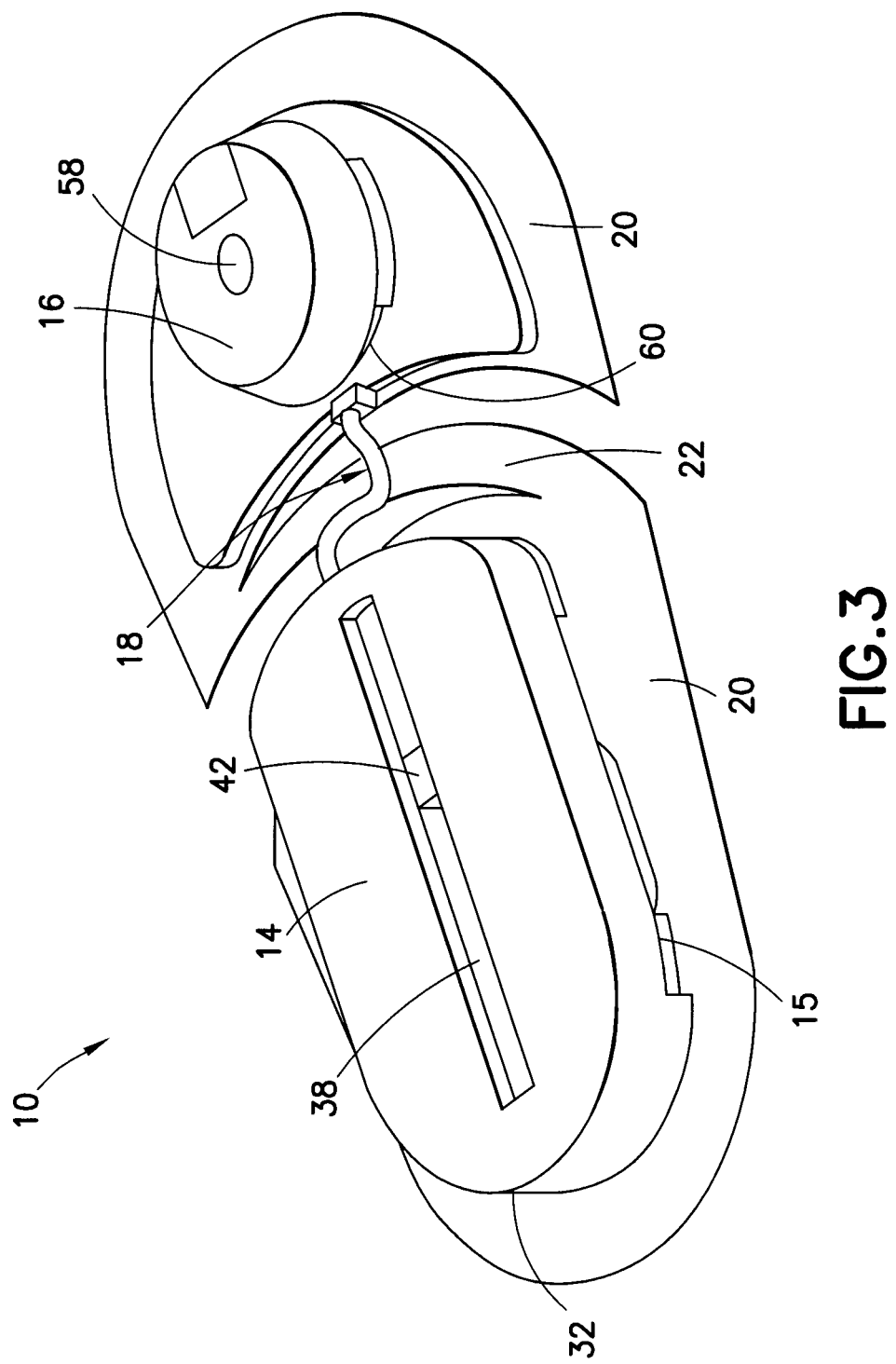
FIG. 3 is a top perspective view of the infusion set of FIG. 1 after activation and removal of the top cover, in accordance with an embodiment of the present invention.

In an exemplary embodiment of the present invention shown in FIGS. 1-3, the device 10 comprises an top cover 12, a main hub 14, and a valve hub 16. A flexible tube 18 is provided for both fluid communication and vibration isolation between the main hub 14 and the valve hub 16. Further, as shown in FIG. 2, a pressure sensitive adhesive layer 20 is provided on a lower surface of both the main hub 14 and the valve hub 16. A tortuous path segment 22 of the adhesive layer 20 is further provided at a position between the main hub 14 and the valve hub 16 for further motion isolation between the main hub 14 and the valve hub 16, and to prevent movement communication between the main hub 14 and the valve hub 16 as described in greater detail below. In exemplary embodiments of the present invention described below, the housings, hubs and other elements can be constructed of a molded plastic material, polycarbonate, polyethylene terephthalate (PET and PTEG), or similar materials.

The top cover 12 comprises an outer surface which a user can grasp, and has an inner opening 25 to slidably cover both the main hub 14 and the valve hub 16. In doing so, the top cover 12 substantially comprises the packaging for containing the device and providing gripping for placement and subsequent activation. The packaging is completed by a covering of the adhesive layer 20.

The adhesive layer 20 is provided with a tab element 24 that extends upward from the skin contact surface as shown in FIG. 1. The tab element 24 can be used to secure the top cover 12, main hub 14 and valve hub 16, together before use. By pulling the tab element 24 free of the device 10, the user can unsecure the top cover 12 and uncover an end of the inner opening 25 to allow the top cover to be slid free of the remaining components once in position, and further pulling the tab element 24 free of the device 10 exposes the pressure sensitive adhesive layer 20 on the lower surface of the main hub 14 and the valve hub 16. The pressure sensitive adhesive layer 20 can comprise any suitable material, such as an adhesive fabric.

The main hub 14 comprises a number of elements contained therein, including an angled stainless steel or plastic needle 26 and slidable needle hub 28 captured in an opening 44. The angled needle 26 and slidable needle hub 28 are in fluid communication and physically coupled with the valve hub 16 via the flexible tube 18, and the tortuous path segment 22 of the adhesive layer 20. As shown in FIG. 2, the main hub 14 also comprises an opening on a lower surface thereof through which the angled needle 26 can be extended for insertion into the skin surface, and having flexible arms 30, which guide the slidable movement of the needle hub 28 and, near an end point thereof, are configured to be deflected by the needle hub 28 and after passage of the needle hub 28, are configured to trap and hold the needle hub 28 in a final position.

In the exemplary embodiment, only a single angled needle 26 is shown, but embodiments of the present invention are not limited thereto. In this or other embodiments, multiple needles can be provided, angled or otherwise positioned. The angled needle 26 can comprise a stainless steel or plastic needle/cannula, between 25 gauge and 36 gauge, provided with a single-bevel, tri-bevel or 5-bevel, but embodiments are not limited thereto. The needle 26 can be bonded to the needle hub 28 with an adhesive, such as a Loctite/UV cured adhesive, or can be overmolded with, or threaded into the needle hub 28. The needle 26 is secured at the desired angle by the slidable needle hub 28, which is in fluid communication with the valve hub 16 via the tubing 18. In an exemplary embodiment of the present invention, the needle 26 is secured at an angle of 20 degrees and extends 4 mm relative to the bottom surface of the main hub 12 and has an overall length of 7 mm relative to the hub 28, to target a depth of 3 mm or less, but embodiments are not limited thereto. In this or other embodiments of the present invention, the needle 26 can be secured at an angle of between 5 degrees and 45 degrees and extend between 3 and 6 mm relative to the bottom surface of the main hub 12 and have an overall length of between 5 and 10 mm relative to the hub 28, and it may be possible to allow for fine adjustments of the angled needle position to target specific depths of infusion in the dermis of subcutaneous layer. Such an angled insertion produces more reliable results for intradermal insertions with a reduced risk of tenting of the skin surface.

The needle hub 28 is configured to be slidable within the main hub 14, as described in greater detail below. At opposite sides of the opening in which the angled needle travels, the lower surface opening of the main hub 142 comprises flexible arms 30, which guide the slidable movement of the needle hub 28 and, near an end point thereof, are configured to be deflected by the needle hub 28 and after passage of the needle hub 28, are configured to trap and hold the needle hub 28 in a final position.

Figure 4:
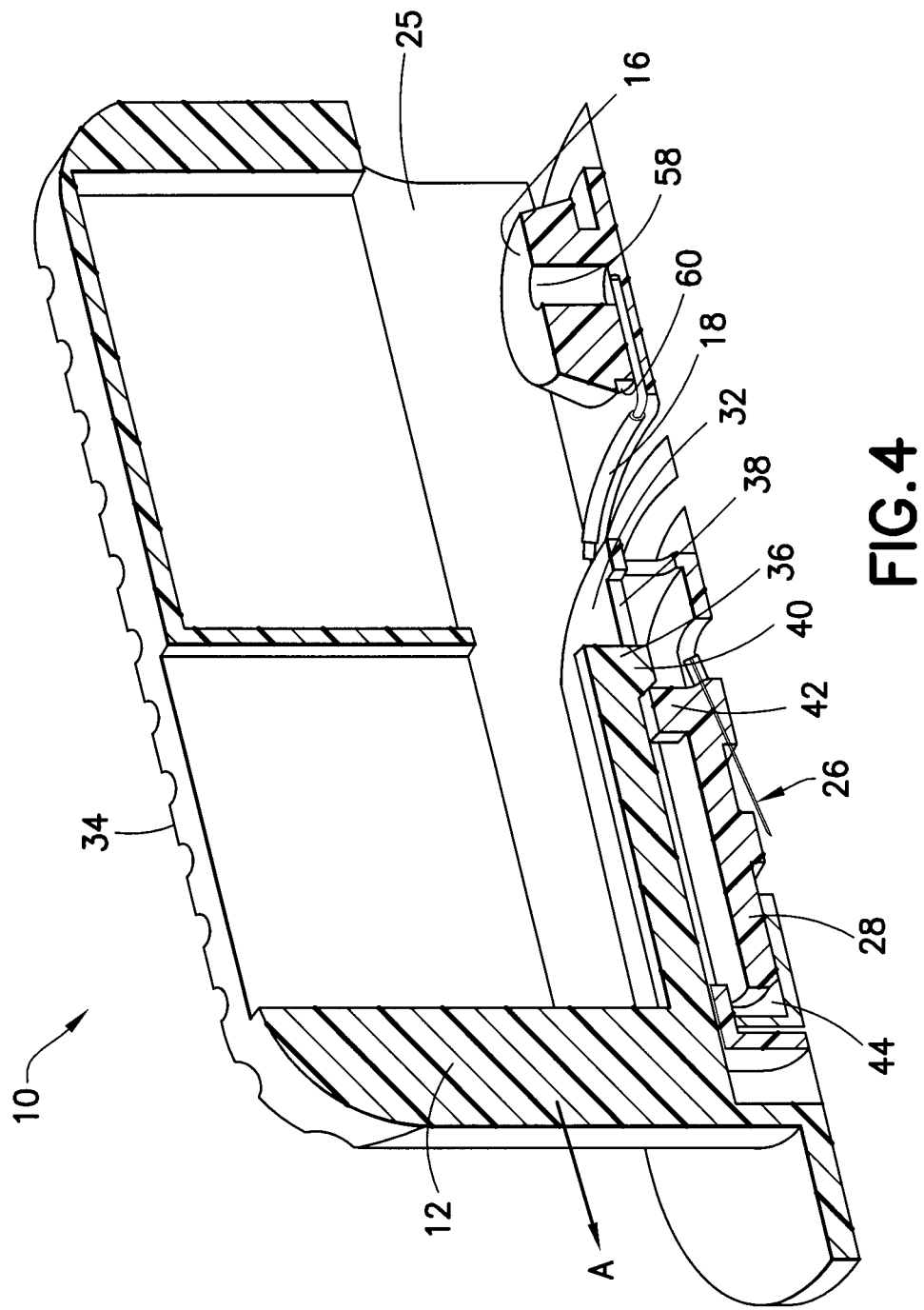
FIG. 4 is a cross-sectional view of the infusion set of FIG. 1 in accordance with an embodiment of the present invention.

As shown in the cross-sectional view of FIG. 4, the main hub 14 further comprises an outer housing 32 upon which the top cover 12 is configured to slide. The main hub 14 can comprise one or more grooves 15 which can slidably capture similar projections on an inner surface of the top cover 12. The top cover 12 is closed at a first end, but opened at a second end as covered by the tab element 24 described above. By pulling the tab element 24 free of the device 10, the user can unsecure the top cover 12 and uncover an end of the inner opening 25 to allow the top cover 12 to be slid free of the main hub 14 and valve hub 16 which are secured to the infusion site.

The top cover 12, which can comprise a textured outer surface 34 to ease gripping, can further comprise one or more drag arms 36 which are configured to extend though an opening 38 in the outer housing 32 of the main hub 14 to pull the needle hub 28 into position. Specifically, the drag arms 36 can comprise one or more detents 40 which are configured to engage one or more detents 42 on the slidable needle hub 28. The needle hub 28 is configured to be slidable within the opening 44 of the main hub 14. As the top cover 12 is pulled in the direction of arrow A and the main hub 14 is secured to the infusion site, the drag arms 36 are configured to pull the slidable needle hub 28 within the opening 44 of the main hub 14. The flexible arms 30 on either side of the opening 44 on the bottom surface of the main hub 14 stick to the skin at the injection site and, as the user pulls the top cover 12 off the device and pulls the needle hub 28 in a direction parallel to the skin surface, the flexible arms 30 move outward when contacted by the moving needle hub 28, thus tensioning, stretching and/or flattening the skin in preparation for needle insertion. When the flexible arms 30 reach their maximum displacement, the angled needle 26 moving with the needle hub 28 penetrates the intradermal layer. Accordingly, when the main hub 14 is secured to a skin surface (not shown), such pulling motion of the top cover 12 is all that is needed to substantially replicate the angled insertion of the Mantoux technique while removing user variability, thereby inserting and anchoring the needle 26 to deliver medicament to the upper 3 mm of skin surface during normal use.

As noted above, the lower surface opening of the main hub 14 comprises the flexible arms 30, which can each comprise an adhesive layer or adhesive pads 46 to secure a portion of each flexible arm 30 to the skin surface at the insertion site. When the device is pressed onto the skin surface, the flexible arms 30 stick to the skin surface at the insertion site. As the user pulls the top cover 12 off of the device, the drag arms 36 extend through the outer housing 32 of the main hub 14 to pull the needle hub 28 in a direction parallel to the skin surface in opening 44, contacting the flexible arms 30 and causing the flexible arms 30 to move outward, thus tensioning, stretching and/or flattening the skin surface to which the flexible arms 30 are secured in preparation for needle 26 insertion.

As shown in FIG. 2, the needle hub 28 is configured to slide within the space 48 between the flexible arms 30. Further, each flexible arm 30 comprises a contour detent 50 which is configured to engage a similar contour end 52 of the needle hub 28 at or near an end of travel of the needle hub 28. Accordingly, as the needle hub 28 is pulled, the contour end 52 of the needle hub 28 engages and deflects the contours 50 causing the flexible arms 30 to move outward, while the adhesive pads 46 of each flexible arm 30 securely hold the skin surface near the insertion site, thus tensioning, stretching and/or flattening the skin surface in preparation for needle 26 insertion. Further, timing of this contact and deflection, is configured to precisely coincide with the timing of the needle 26 insertion to maximize beneficial effects.

When the flexible arms 30 reach their maximum displacement, the angled needle 26 penetrates the intradermal layer. As the needle 26 and needle hub 28 are dragged to the end stop contained within the outer housing 32 of the main hub 14, the needle hub 28 clears the contours 50 allowing the flexible arms 30 to retract behind the needle hub 28, creating a passive snap which holds the inserted needle hub 28 in its final position and holding the inserted needle 26 in place.

Further, the use of an angled needle 26 in the embodiments of the present invention provides another solid anchor which maintains the infusion site. Typically, it is very difficult to maintain the position of small (i.e., 1-3 mm) needles within the skin. However, by angling the needle, the skin itself provides vertical retention force. Accordingly, the inserted needle is secured both vertically and horizontally. Further, an angled insertion allows for more flexibility of needle or cannula choice for infusion by reducing the vertical height of the cannula opening. Also, since the needle is inserted at an angle, a longer needle and/or needle opening can be used than those provided for a non-angled insertion to target the same intradermal depth.

Figure 5:
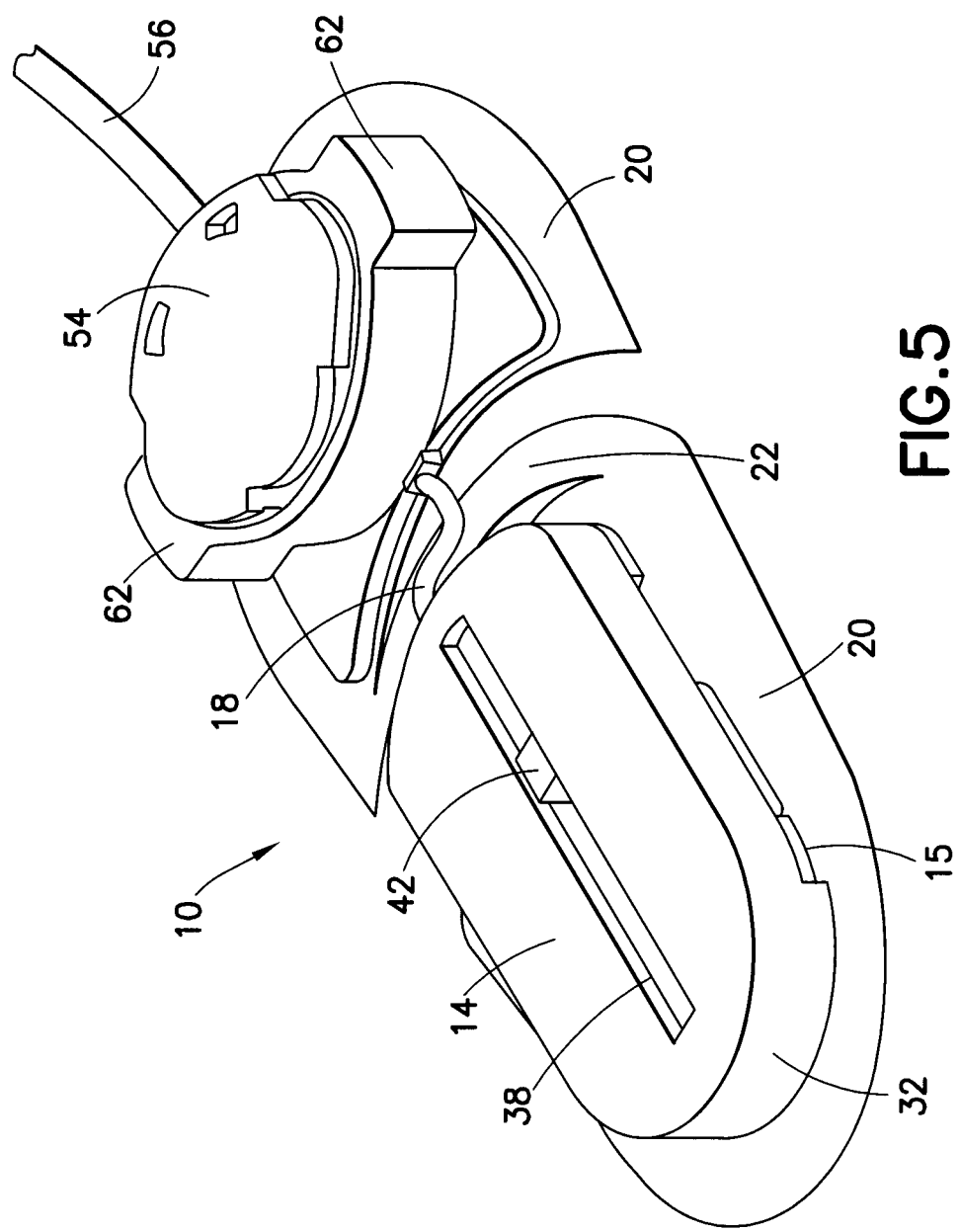
FIG. 5 is a top perspective view of the infusion set of FIG. 1 after activation and removal of the top cover, and assembly with a pump interface connector, in accordance with an embodiment of the present invention.

With the needle 26 properly inserted and the top cover 12 removed and discarded, the user can then attach a pump interface connector 54 and tube set 56 to the valve hub 16 as shown in FIG. 5 using, for example, flexible plastic snaps to capture grooves 60 on the valve hub 16. The pump interface can comprise a piercing member (not shown) to pierce a centrally-positioned septum or other valve member 58 of the valve hub 16 which is in fluid communication with the flexible tube 18. In doing so, the pump interface connector 54 and tube set 56 are configured to allow rotation with up to 180-270 degrees of rotation about the valve hub 16, which helps in tubing placement. The pump interface connector 54 can further comprise a flexible body with one or more pushable portions 62 which can be squeezed by a user to release the flexible plastic snaps from the grooves 60 on the valve hub 16, and permit removal of the pump interface connector 54 and tube set 56.

As shown in FIG. 3, with the top cover 12 removed, both the main hub 14 and the valve member 58 of the valve hub 16 are revealed, and the user can connect the insulin pump to the valve hub 16 and commence fixed priming of the infusion set. The angled needle 26 and slidable needle hub 28 of the main hub 14 are in fluid communication and physically coupled with the valve hub 16 via the flexible tube 18, and the tortuous path segment 22 of the adhesive layer 20. After priming, standard delivery of insulin to the infusion set is provided. To allow for priming of the exemplary infusion sets before needle insertion, it is possible to remove a portion of the top cover 12, allowing valve connection access.

The needle 26 is protected from external forces and motions by the outer housing 32 of the main hub 14, and the isolation of the main hub 14 from the valve hub 16 by the tube connection 18 and a spiral cut segment 22 of the adhesive between the main hub 14 adhesive and the valve hub 16 adhesive. That is, the angled needle 26 and slidable needle hub 28 of the main hub 14 are in fluid communication and physically coupled with the valve hub 16 only via the flexible tube 18, and the tortuous path segment 22 of the adhesive layer 20, to isolate the angled needle 26 and slidable needle hub 28 of the main hub 14 from unwanted movement. By carefully isolating the needle hub 28 and the needle 26 from external forces, the needle position within the intradermal layer is maintained.

Also, by first adhering the main hub to the skin surface, a precise mechanical foundation is provided which ensures that the needle angle, skin tensioning, stretching and/or flattening, and insertion depth are consistent. Further, in doing so, tenting is also reduced or eliminated. Still further, by isolating the needle site for the pump connection, vibrations and movements are reduced. In addition, a low-profile is provided which further isolates the needle from any external forces.

Currently, there are no such intradermal insulin infusion devices, yet, as noted above, intradermal delivery can be accomplished with the standard Mantoux technique. However, this method is highly variable and subject to user error. In addition, there are several "patch" injection systems which deliver into the intradermal space. However, these systems may have difficulty providing a solution for long-term (i.e., three day) insulin infusion. By providing a system and method which essentially reduces the Mantoux technique to a standardized process and removing user variability, the exemplary embodiments of the present invention provide a practical solution for inserting and anchoring a needle, preferably to deliver content to the upper 3 mm of skin surface during normal use, delivering insulin into the intradermal space.

In mimicking the Mantoux technique in such a way, the needle insertion can be accomplished with a simple user motion. The exemplary embodiments of the present invention standardize the Mantoux technique, which currently is a desirable, but highly variable means of injecting into the intradermal layers of skin. When administered correctly, the Mantoux technique nicely injects the medicament into the intradermal space. By eliminating the variability in this preferred technique, a reliable proven means of infusion is established.

The exemplary embodiment described above performs a needle insertion using a user-controlled sliding action of the top cover during removal. Some other infusion sets require ballistic insertion into the skin in which a compression or flexed plastic spring forcefully drives the needle. These insertion methods can require cumbersome insertion devices which oftentimes are separate from the infusion set. In the exemplary embodiments described above, the user simply pulls off the top cover, which stretches and/or flattens the skin surface, or otherwise creates skin tension, and drives the needle downward in a manner identical to the Mantoux technique. By eliminating insertion devices, the user will not be forced to use a set that the user cannot insert, and by inserting via the Mantoux technique, the overall device profile remains small and not cumbersome.

By infusing into the intradermal layer of the skin, the exemplary embodiments of the present invention offer the potential for better absorption of the insulin when compared to subcutaneous delivery systems. In doing so, it may be possible for the typical user to both consume less insulin and maintain a better medicament regime. It will be appreciated that multiple needles or microneedles can be used, if desired, in place of a single needle or microneedle.

As noted above, other intradermal infusion set concepts are at risk of tenting, which is the undesired effect where skin is deflected at or during insertion, creating a shape associated with a tent in the skin surface at the point of needle insertion. In doing so, the skin surface tents during needle insertion rather than needle penetration into the skin. However, since the present invention provides a needle which is inserted at a controlled angle, and wherein the skin surface is secured, tensed, stretched, and/or flattened at the insertion site, the exemplary embodiments of the present invention reduce this risk and ensure more precise needle insertion depth.

In current steel cannula infusion sets which deliver to the subcutaneous layer, the needle is not isolated from any undesired outside forces which may cause pain when translated to the needle and the needle moves within the skin. Also, other intradermal devices face problems of premature or otherwise undesired needle removal when the device is bumped, if the needle is not isolated form the outside forces.

In the exemplary embodiments of the present invention, the intradermal needle is isolated from outside forces by multiple features. First, the outer housing 32 of the main hub 14 shields the sensitive needle 26 and needle hub 28 from direct contact with external forces. Second, connections 18 and 22 between the main hub 14 and the valve hub 16 are extremely flexible, so that any forces imparted on the valve hub 16 do not carry over to the needle 26. For example, the provision of the flexible tubing connection 18 and tortuous path segment 22 of the adhesive layer 20, serve to effectively isolate the needle 26 from the outside forces and other interference.

Proper alignment is accomplished by providing a solid, fixed foundation for the user to slide the outer housing 12 and insert the angled needle 26. Such a solid, fixed foundation is provided by the adhesive layer 20. The skin adhesive layer secures the set 10 at a desired orientation, such that the needle hub 28 and angled needle 26, and the top cover 12 are at a desired orientation of use, and the user is substantially prevented from holding the device at angles to the insertion site. Accordingly, precise, repeatable insertions are accomplished.

Still further, many commercial sets require the use of a separate auto-inserter. In the exemplary embodiments of the present invention described herein, the user does not have to carry a separate inserter or load the infusion set onto the inserter. The integrated system allows the user more freedom from carrying and loading a separate inserter resulting in improved convenience and simpler operation.

However, similar benefits can exist with the proper implementation of ballistic insertion of the needle into the skin. For example, in the following embodiment of the present invention, a sliding action can also be used in cooperation with a ballistic insertion to reduce the risk of tenting and ensure more precise needle insertion depth. By utilizing a top cover to load and then release a needle-driving cantilever beam, and an isolated needle hub, proper insertion and maintenance of the inserted needle in the intradermal space is ensured.

Figure 6:
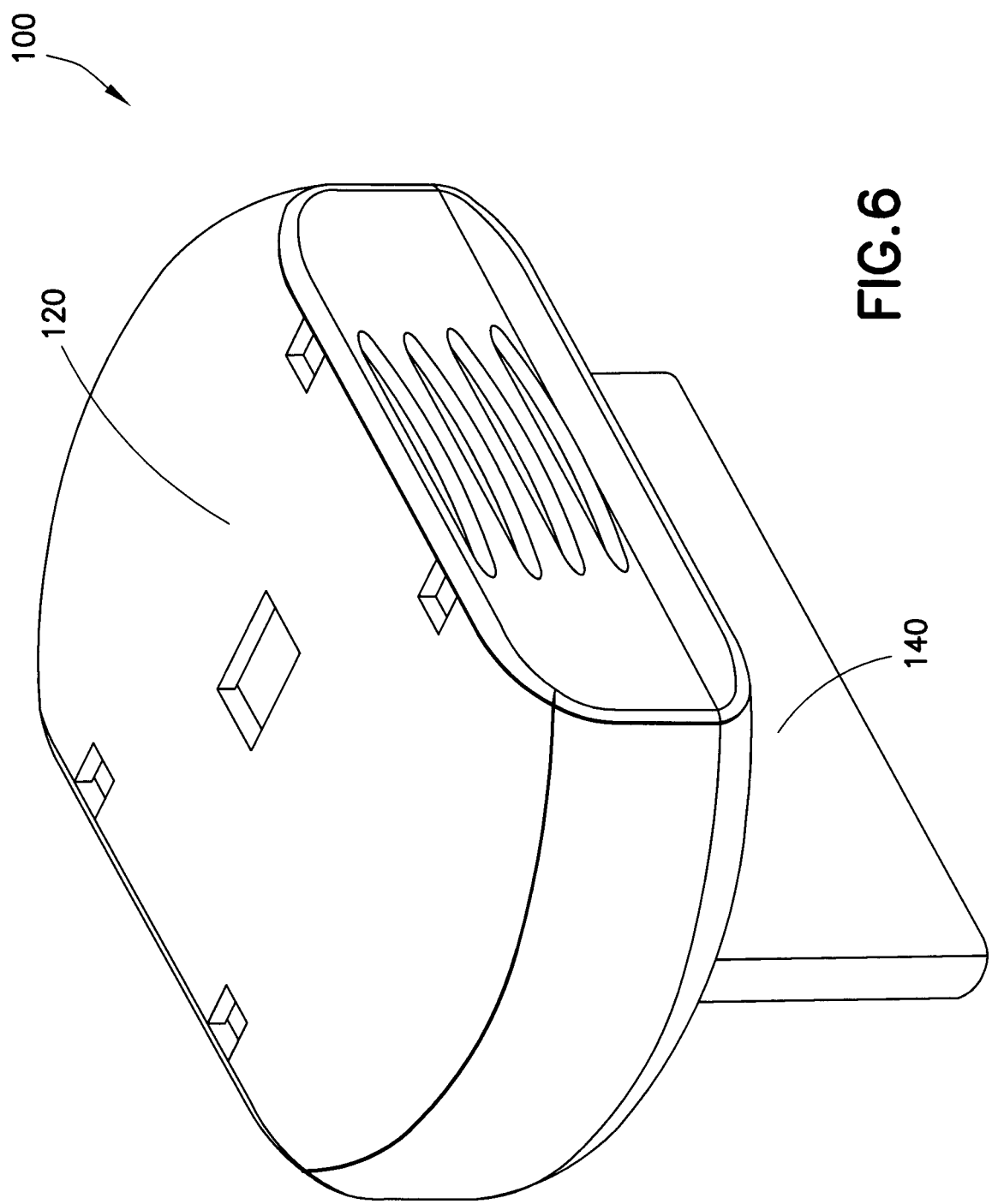
FIG. 6 is a perspective view of an infusion set which can include one or more exemplary elements in accordance with another embodiment of the present invention.
Figure 7:
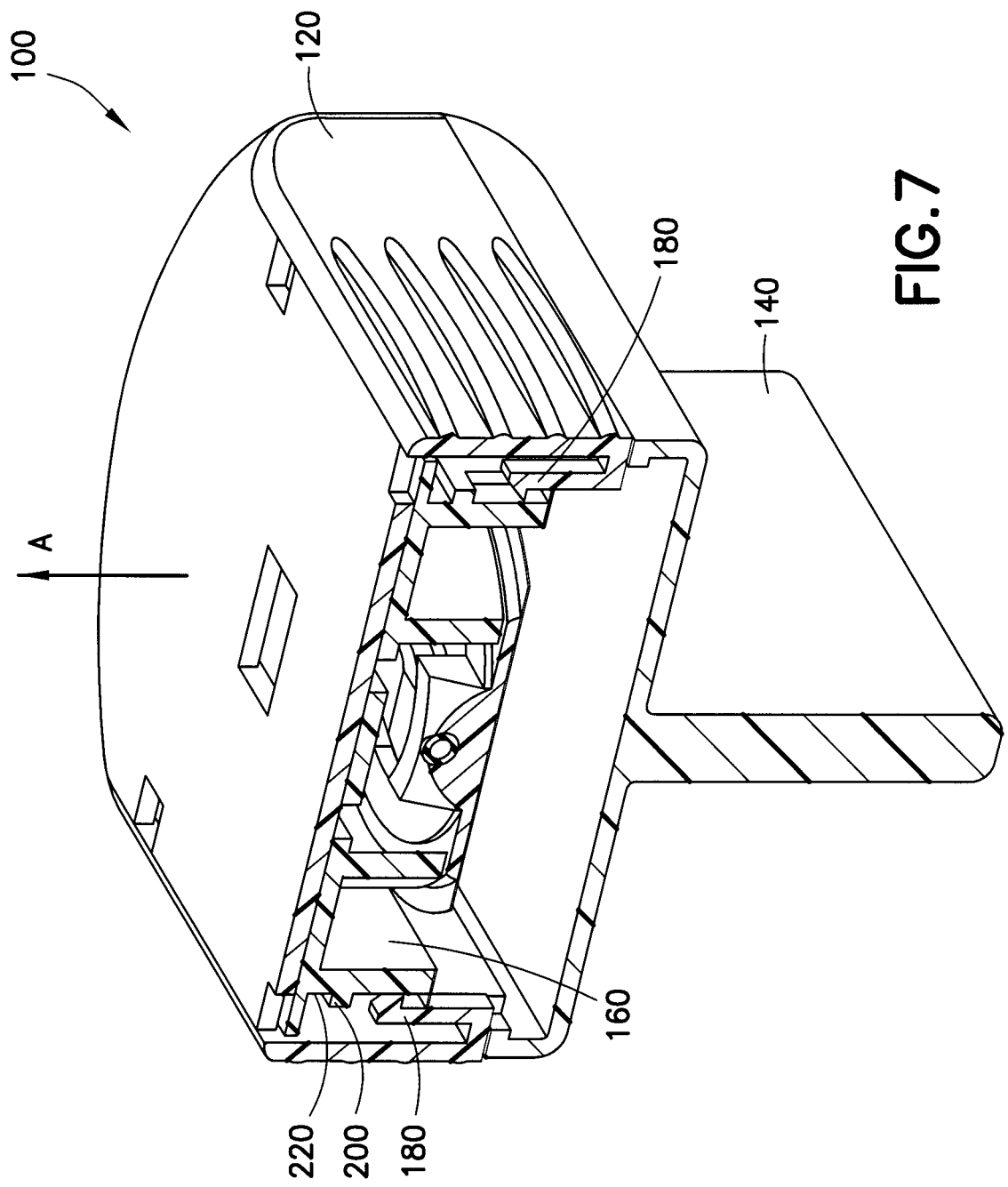
FIG. 7 is a cross-sectional view of the infusion set of FIG. 6 in accordance with an embodiment of the present invention.

FIGS. 6 and 7 illustrate another exemplary infusion set 100 including the following features. As shown in FIGS. 6 and 7, the exemplary infusion set 100 can comprise a top cover 120, a bottom cover 140, and an outer hub 160 captured therebetween. The top cover 120 is configured to be releasably secured to the bottom cover 140, and can be removed from the bottom cover 140 with an upward pulling motion as shown by arrow A in FIGS. 7 and 8. During removal of the top cover 120, a number of activation features are engaged. In exemplary embodiments of the present invention described below, the covers, hubs and other elements can be constructed of a molded plastic material, polycarbonate, thermoplastic polymer such as polyethylene terephthalate (PET and PETG), or similar materials.

Figure 8:
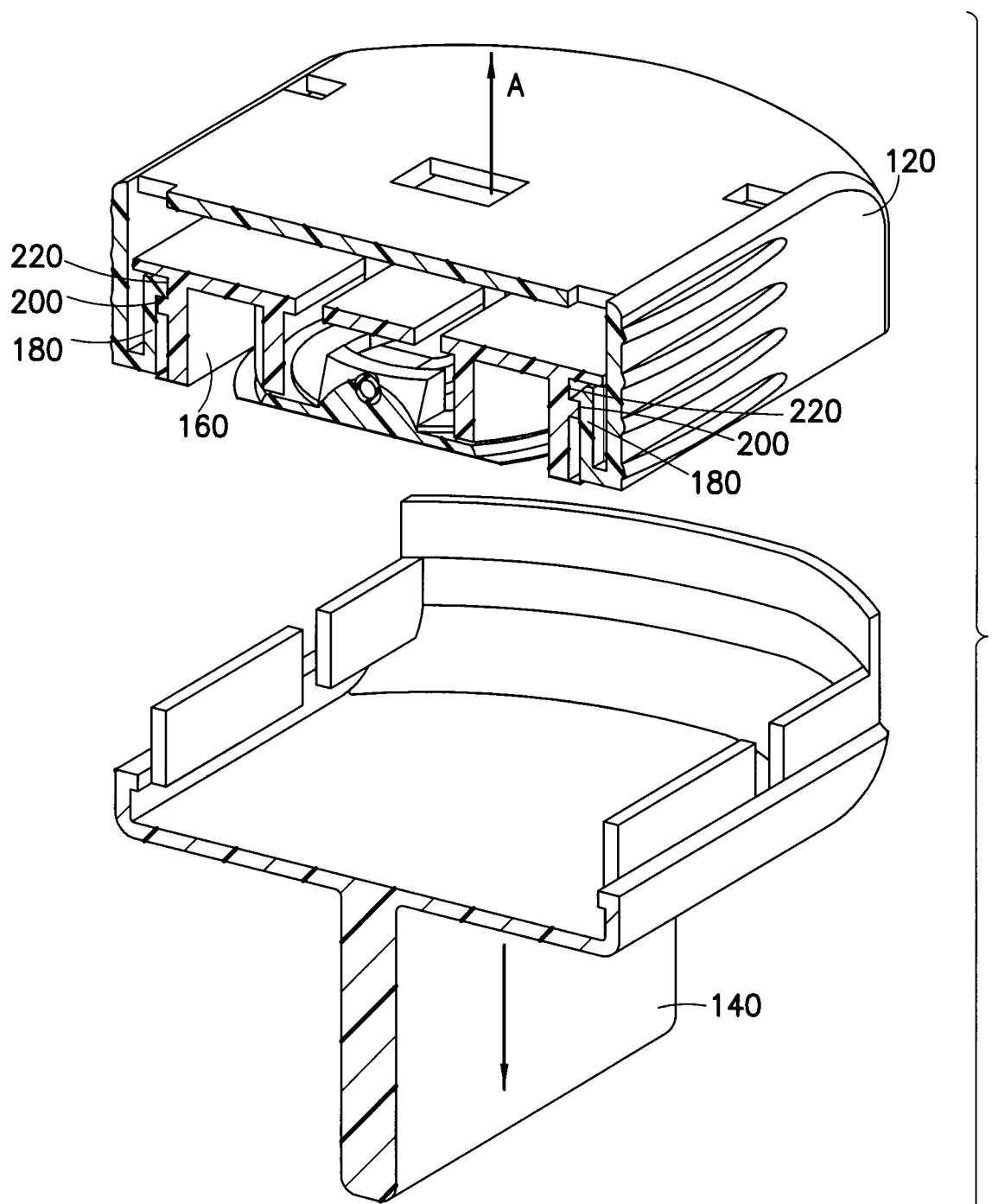
FIG. 8 is a cross-sectional view of the infusion set of FIG. 6 showing the top cover and infusion set being removed from the bottom cover in accordance with an embodiment of the present invention.
Figure 9:
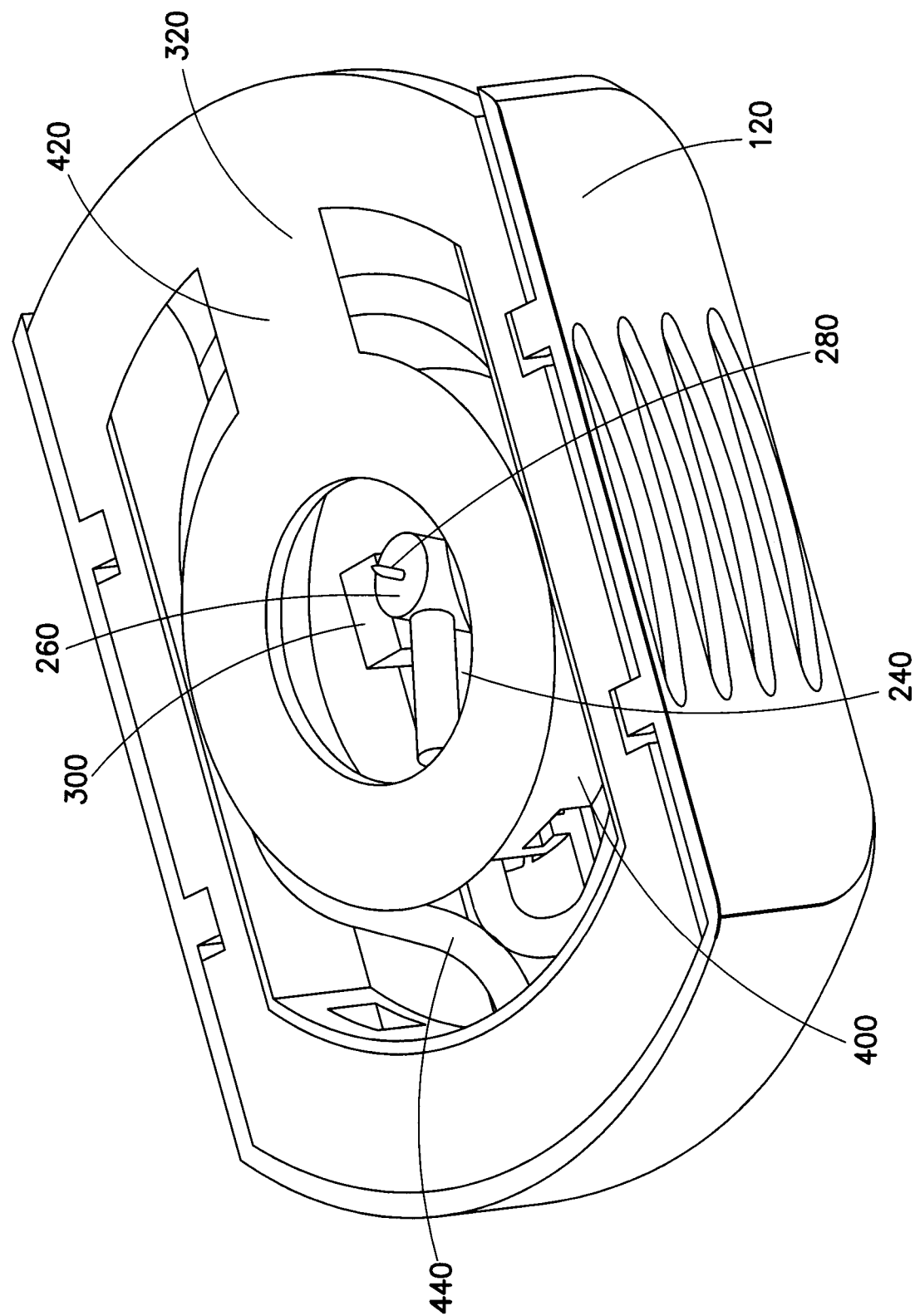
FIG. 9 is a perspective bottom view of the top cover and infusion set of FIG. 8 in accordance with an embodiment of the present invention.

As the top cover 120 is pulled away from the bottom cover 140, the outer hub 160 is held briefly by the bottom cover 140 such that the top cover 120 is first slidably pulled some distance relative to the outer hub 160 captured between the top cover 120 and the bottom cover 140. As the top cover 120 is pulled, a plurality of deflectable snaps 180 disposed within the top cover 120 are slid with the top cover while the outer hub 160 remains held by the bottom cover 140. An incline on each snap 180 eventually contacts a shoulder 200 on an outer surface of the outer hub 160, thereby deflecting the snaps 180 outward and allowing the snaps 180 to pass over the shoulder 200 and become trapped in a channel 220 as shown in FIG. 8. As described in greater detail below, the snaps 180 can slide within the channel 220 in directions perpendicular to the direction of arrow A to allow movement of the top cover 120 and specifically, slidable movement of the top cover 120 from the outer hub 160.

As shown in FIG. 8, once the snaps 180 of the top cover 120 are trapped in the channel 220 of the outer hub 160, further pulling of the top cover 120 away from the bottom cover 140 serves to pull the outer hub 160 with the top cover 120 in the direction of arrow A, and separate the top cover 120, containing therein the outer hub 160, from the bottom cover 140. The bottom cover 140 can then be discarded. In yet other embodiments of the present invention, the bottom cover 140 is saved for re-attachment of the set after use for safe, shielded needle disposal. The bottom cover 140 can be saved for re-covering the exposed needle 280 of the same or previously-used set for safe disposal.

As next shown in FIGS. 9-12, the outer hub 160 covers and contains therein an inner hub 400 which contains a cantilevered needle and needle hub, in fluid communication with a valve connection septum via a flexible tube. Specifically, the inner hub 400 includes at least one cantilever beam 240, needle 280 and needle hub 260, in fluid communication with a valve connection septum 360 via a flexible tube 440. The inner hub 400 is connected with the outer hub 160 by only the flexible member 420, and the flexible tube 440. The needle 280 of the inner hub 400 can have an overall length of between 3 and 10 mm to target a depth of 3 mm or less, and can comprise a stainless steel or plastic needle, between 31 gauge and 34 gauge, provided with a single-bevel, tri-bevel or 5-bevel, and be between 1.0 and 10 mm long, but embodiments are not limited thereto. The needle 280 can be bonded to the needle hub 260 with an adhesive, such as a Loctite/UV cured adhesive, or can be over-molded with, or threaded into the needle hub 260. Only one cantilever beam 240 and needle 280 are shown. However, in other exemplary embodiments of the present invention, a plurality of cantilever beams and/or needles can be provided. Connection between the outer hub 160 and needle 280 is provided by the flexible tube 440 extending from the needle hub 260 and deflectable with the cantilever beam 240, through the inner hub 400, and to the valve connection septum 360 of the outer hub 160 for fluid communication. A loop of the flexible tube 440 can be provided in the space between the inner and outer hubs to provide further flexibility and isolation.

Figure 10:
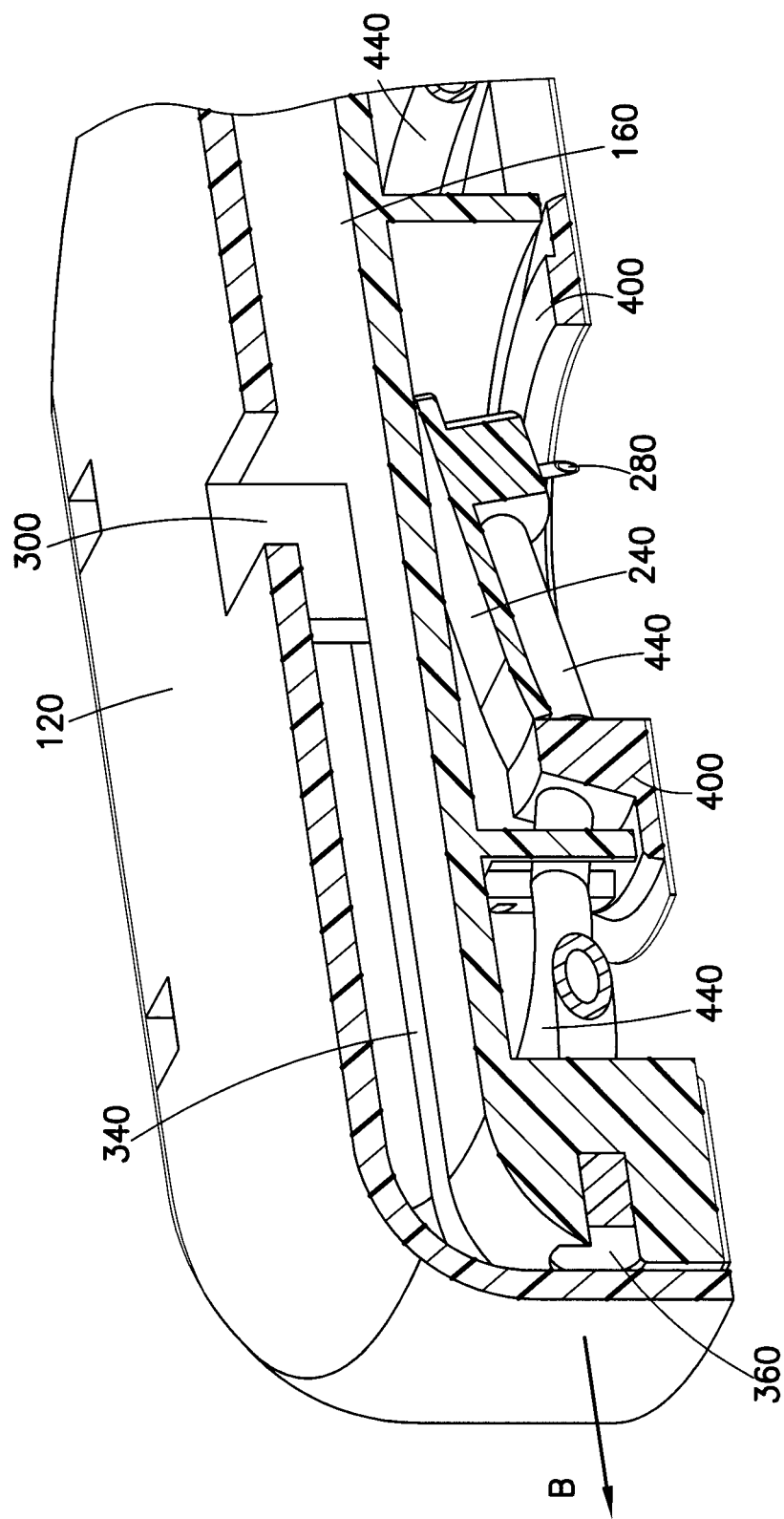
FIG. 10 is a cross-sectional view of the top cover and infusion set of FIG. 8 prior to activation and removal of the top cover in accordance with an embodiment of the present invention.

The top cover 120 further comprises one or more beam hanger arms 300 which extend through slotted openings 340 in the top surface of the outer hub 160 to engage the cantilever beam 240 of the inner hub 400. As the top cover 120 is pulled away from the bottom cover 140 in the direction of arrow A, at least one beam hanger arm 300 of the top cover 120, having a detent, shoulder or other feature at an end thereof, is configured to reach through slots 340 in the top surface of the outer hub 160, capture the cantilever beam 240 of the inner hub 400, and preload the cantilever beam 240 when the top cover 120 is removed in the direction of arrow A. The movement of the beam hanger arm 300 serves to pull, deflect and/or load the cantilever beam 240 of the inner hub 400 as shown in FIG. 10. The complete deflection and loading position of the cantilever beam 240 by the beam hanger arm 300 is configured to occur substantially at the point where the snaps 180 become trapped in the channel 220 of the outer hub 160 as described above. In such a position, the top cover 120 and outer hub 160 are prevented from any further movement, forward or backward in the direction of arrow A. As such, the top cover 120 and outer hub 160 can be safely handled without risk of needle discharge or relaxation of the cantilever beam 240.

Figure 11:
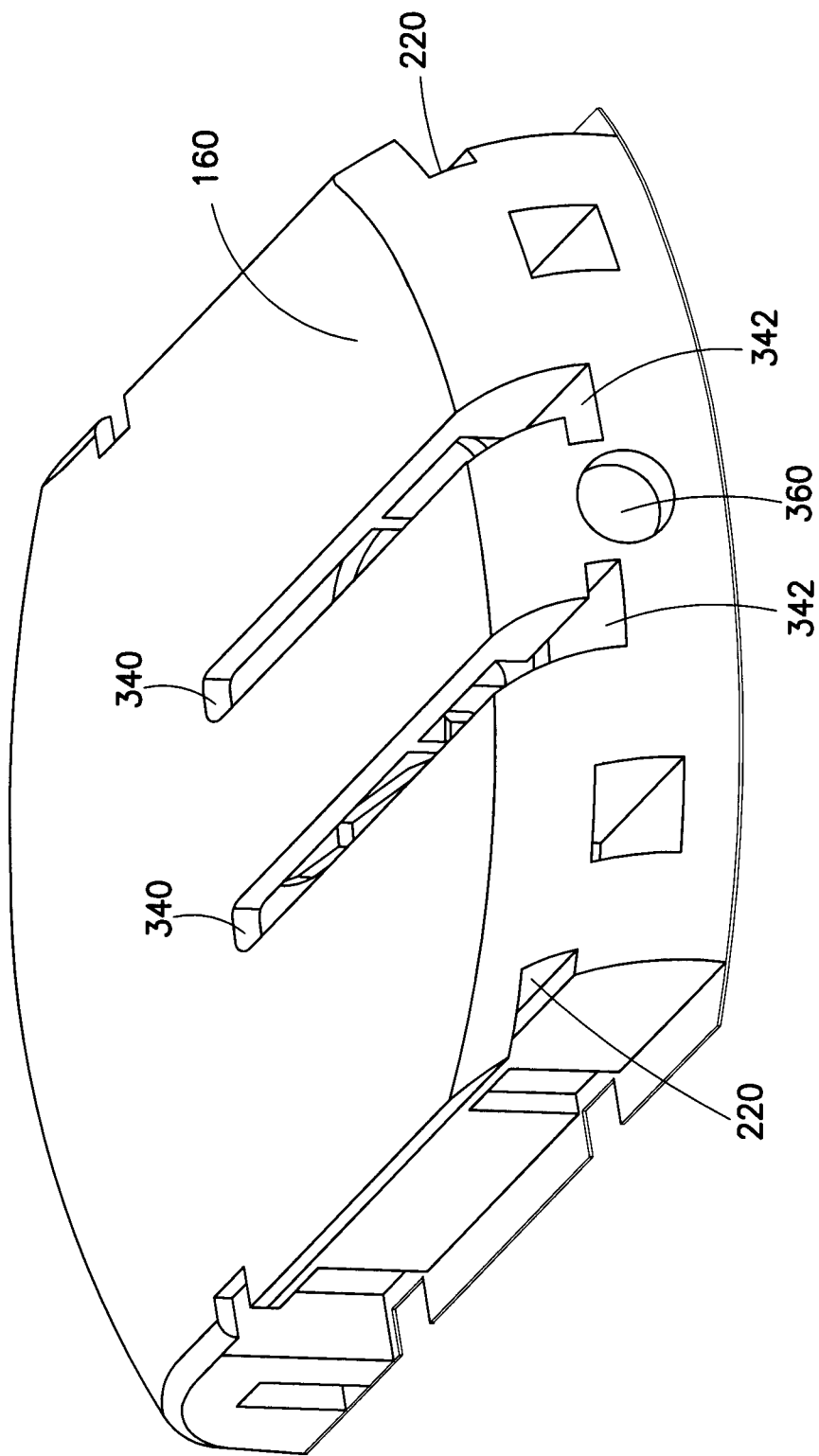
FIG. 11 is a perspective top view of the infusion set of FIG. 8 after removal of the top cover and activation in accordance with an embodiment of the present invention.
Figure 12:
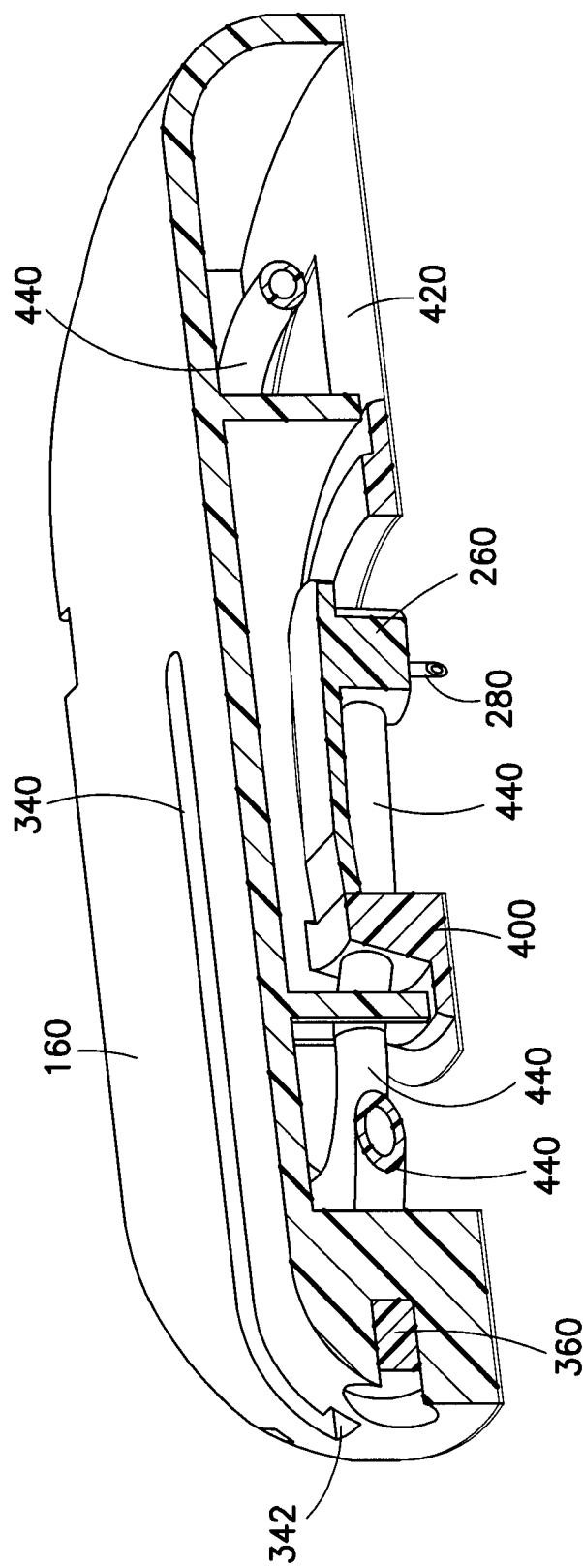
FIG. 12 is a cross-sectional view of the infusion set of FIG. 11 after removal of the top cover and activation in accordance with an embodiment of the present invention.
Figure 13:
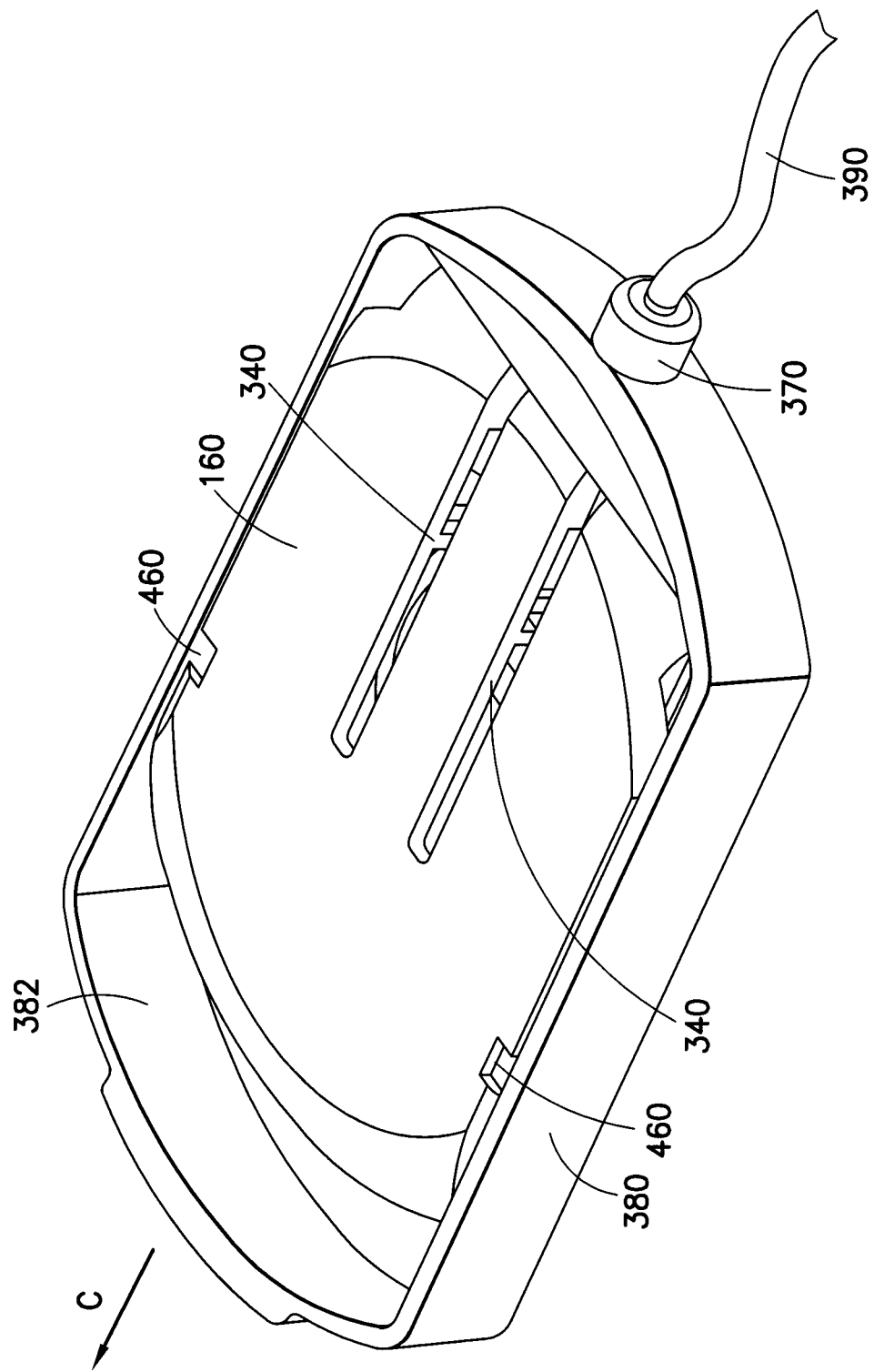
FIG. 13 is a perspective top view of the infusion set of FIG. 11 after attachment of the valve connector in accordance with an embodiment of the present invention.

At this time, the user can apply the top cover 120 and outer hub 160 therein to a skin surface (not shown). An adhesive layer 320 can be provided upon a bottom surface of the outer hub 160 and inner hub 400 to secure the outer hub 160 and the inner hub 400 to the skin surface. Once in position, the top cover 120 can be slid relative to the outer hub 160 and inner hub 400 as shown by arrow B in FIG. 10. The snaps 180 trapped in the channel 220 of the outer hub 160, guide the slidable removal of the top cover 120 from the outer hub 160 and inner hub 400, leaving the outer hub 160 and inner hub 400 in place as shown in FIG. 11. Further, the beam hanger arm 300 of the top cover 120 is slidably pulled with the top cover 120 relative to the outer hub 160 and inner hub 400, as permitted by the slots 340 in a top surface of the outer hub 160 as shown in FIG. 11. As the beam hanger arm 300 of the top cover 120 is slidably pulled away from the cantilever beam 240 of the inner hub 400 through slots 340 of the outer hub 160, the cantilever beam 240 is released, thereby inserting the needle 280 at a high rate of speed thereby minimizing tenting, into the insertion site at the desired depth. An exemplary embodiment of the present invention is configured to insert the needle 280 at a controlled high rate of speed, of 3.3 ft/sec. (1.0 m/sec.) up to and including those greater than 10 ft/sec. (3.0 m/sec.). Depending upon cannula sharpness, such a terminal velocity produces more reliable results for intradermal insertions of short (i.e., 1.5 mm) needle or cannula with a reduced risk of tenting of the skin surface. The slots 340 in the outer hub 160 are open at ends 342 to allow the complete slidable removal of the top cover 120, including beam hanger arm 300, from the outer hub 160.

The now-exposed top surface of the outer hub 160 as shown in FIG. 11 allows access to the valve connection septum 360 for receiving a piercing member (not shown) of a circular valve connector 380. The valve connector 380, with tube connector 370 and tube 390, can be placed over the outer hub 160 and slid in the direction of arrow C to engage the valve connection septum 360 which then connects the outer hub 160 to an infusion pump or other insulin supply (not shown) and provides for fluid communication between the infusion pump reservoir and the device.

Needle isolation is accomplished via a number of isolating mechanisms. First, the outer hub 160 and valve connector 380 of the device serve as a protective cover and as an element which isolates the inner hub 400 from external forces. Second, the inner hub 400 is provided within the outer hub 160 and specifically, the sensitive needle 280 and cantilever beam 240 of the inner hub 400 is shielded by the inner hub 400 from external forces to provide even further isolation. Third, the inner hub 400 is connected with the outer hub 160 via only the flexible member 420 and tube 440. To further isolate vibrations and external forces, the adhesive under the inner hub 400 is connected to the adhesive under the outer hub 160 via the thin, strain-relieving segment 420, and the fluid communication between the inner hub 400 and the outer hub 160 is provided via the flexible tube 440, so any forces imparted on the outer hub 160 and valve connector 380 do not carry over or transmit to the needle 280 of the inner hub 400. Fourth, the flexible tube 440 is provided from the needle hub 260, looping the inner hub 400, and to the valve connection septum 360 of the outer hub 16 for fluid communication. The relative flexibility of this looped tubing serves to further isolate the two hubs from one another.

In an exemplary use of the device, the user first pulls apart the top and bottom covers 120 and 140 as shown. The bottom cover 140 separates from the device after the top cover 120 snaps into the outer hub guide tracks 220 of the outer hub 160, and the cantilever beam 240 is loaded. As the bottom cover 140 separates from the top cover 120 and outer hub 160, a skin adhesive 320 is exposed on the bottom surface of the outer hub 160.

The user can now place the device on the infusion site. By pulling the top cover 120 sideways off the outer hub 160, the cantilever beam 240 is released and the needle 280 is discharged into the skin surface. In an exemplary embodiment of the present invention, the needle 280 is inserted and held within the top 3 mm of the skin surface, but the present invention is not limited thereto. As noted above, insertion of the needle into the top 3 mm of the skin surface, the intradermal space facilitates better drug absorption while maintaining a degree of comfort to the user.

With the top cover 120 removed, the user can then attach the valve connector 380 for connection with an infusion pump. With a fixed prime, the device is then ready to infuse insulin at the desired depth and rate. In another exemplary embodiment of the present invention, to allow for priming of the set before needle insertion, it is possible to remove a portion of a modified top cover (not shown), allowing access to the valve connection septum 360 of the outer hub 160.

As noted above, the cantilever beam within the device is first loaded and then fired by the user, since storing a preloaded beam would subject the device to plastic relaxation. To do so, as the user pulls apart the covers, arm(s) on the top cover pull back the cantilever beam, which is centrally mounted underneath the outer hub. The operation of the cantilever beam is described through the Euler-Bernoulli beam theory, or engineer's beam theory, classical beam theory or beam theory, which provides a means of calculating the load-carrying and deflection characteristics of a beam structure.

On an outer surface of the outer hub 160 lies guide tracks 220, which stop the top cover 120 vertically, along with the outer hub 160, when the cantilever beam 240 is properly stressed. At this end stop, the top cover 120 locks vertically, the bottom cover separates 140 from the device, and the skin adhesive 320 is revealed.

Once in position, with the device adhered to the infusion site, the top cover 120 can then be pulled along the guide tracks 220 in a direction noted by arrows B. As the top cover 120 is pulled away, the arms 300 holding the cantilever beam 240 clear its side tabs, which allow the cantilever beam 240 to discharge and drive the insertion needle 280 into the skin. Although only a single insertion needle is shown, the present invention is not limited thereto.

The cantilever beam 240 is designed to contain a small preload, which would maintain a small compression force on the infusion site even after insertion. This force on the skin serves to maintain needle position over time. Such a localized preload force maintains needle depth within the skin. This added pressure maintains the contact between the needle hub 260 and the skin. Therefore, the needle 280 is maintained at a precise depth in the intradermal layers of skin. In a preferred embodiment of the present invention, such depth is within the top 3 mm of the skin surface.

In this or other exemplary embodiments of the present invention, the cantilever beam can be loaded and held by opposing arm elements to balance the delivery. Further, the angle of the needle hub can be changed in this or other exemplary embodiments of the present invention to affect the insertion angle and final placement of the needle. In these or other embodiments of the present invention, the cantilever beam can be constructed of a plastic, metal or other resilient material including, for example, a molded plastic material, polycarbonate, thermoplastic polymer such as polyethylene terephthalate (PET and PETG), or similar material.

The circular valve connector 380 is placed over the outer hub 160 vertically, and then slid horizontally in the direction of arrow C. The horizontal movement of the valve connector 380 drives a piercing member (not shown) into the septum valve 360, and snaps 460 are provided along inner walls to engage detents in the outer hub 160 and snap the valve connector 380 into place. The valve connector 380 may be removed with one hand by pushing the side opposite the septum valve 360 as permitted by space 382, which causes snaps 460 of the valve connector 380 to flex and release. The valve connector 380 type can have a variety of embodiments to allow for rotation, anchoring, ease of use, and other desirable features and functions.

Currently, there are no intradermal insulin infusion devices on the market because a robust means of inserting and maintaining needle position within the intradermal layer is extremely difficult. But utilizing a simplified cantilever beam to store energy within the device, insertion and needle maintenance are accomplished in a simplified manner. The cantilever beam itself is protected from any external forces and vibrations by the outer hub. By carefully isolating the inner hub and the cantilever beam from the external forces, the needle position within the intradermal layer is maintained.

Further, by infusing into the intradermal layer of the skin, the exemplary embodiments of the present invention offer the potential for better absorption of insulin when compared to subcutaneous delivery systems. In doing so, it may be possible for the typical user to both consume less insulin and maintain a better medicament regime.

As noted above, other intradermal infusion set designs are at risk of "tenting", which is the undesired effect where skin is deflected at needle insertion before or during insertion, creating a shape similar to a tent. In doing so, the skin surface tents during needle insertion rather than needle penetration into the skin. However, since an adhesive layer is provided and rapid needle insertion is provided via the activated cantilever beam, the risk of tenting or skin deflection otherwise affecting final insertion depth is reduced. Still further, a small intradermal needle placed perpendicular to the skin and isolated from outside forces causes less pain to the user during use.

Still further, most infusion sets currently on the market require an inserter. The inserter is typically a throw-away or disposable piece of the device packing, or an inexpensive second part of the set. However, in exemplary embodiments of the present invention described above, the insertion can be fully integrated into the single device through the use of the cantilever beam, and top and bottom covers. In the exemplary embodiments of the present invention described herein, the user does not have to carry a separate inserter or load the infusion set onto the inserter. The integrated system allows the user more freedom from carrying and loading a separate inserter resulting in improved convenience and simpler operation. Typical devices of the market use relatively large external inserters to fire the needle into the skin. In contrast, exemplary embodiments of the present invention provide the advantage of utilizing the flexed cantilever beam wherein loading and release are incorporated into cover removal steps and wherein such covers can then be discarded. In doing so, the top covers can function as a removable inserter. Such a system and method is economical, simple, and compact, and provides a system of insertion that is integrated with the device. Therefore, a user can correctly insert the device without an additional tool.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

What is claimed is:

1. An infusion set configured to be secured to a skin surface for targeting a desired depth to deliver content to an upper skin surface, comprising:
    a slidable top cover enclosing:
        a main hub configured to be secured to said skin surface, said main hub including an insertion track; and
        a needle hub fixed to a needle, a base of said needle being configured to pivot while traveling during insertion on said insertion track as urged by a motion from a user; wherein
    said needle is configured to assume a first angle relative to said skin surface in a free state;
    when said main hub is secured to said skin surface, said needle deflects at an angle relative to said skin surface that is different from said first angle of said needle;
    said motion is applied to said needle to insert said needle into said skin surface; and
    said needle returns toward said first angle relative to said skin surface during said motion.

2. An infusion set as claimed in claim 1, wherein:
    wherein said needle is configured to assume a second angle relative to said skin surface when said main hub is secured with said skin surface but prior to application of said motion; and
    wherein said needle is configured to assume a third angle relative to said skin surface during application of said motion.

3. An infusion set as claimed in claim 2, wherein a difference between the first angle and third angle is smaller than a difference between the second angle and the third angle.

4. An infusion set as claimed in claim 2, wherein the first angle and the third angle relative to the skin surface are substantially similar.

5. An infusion set as claimed in claim 2, wherein the angle of the motion is different than the second and third angle of the needle relative to the skin surface.

6. An infusion set as claimed in claim 1, wherein the insertion track being substantially parallel to the skin surface.

7. An infusion set as claimed in claim 6, wherein the motion is applied by the user in the direction of the insertion track when the needle enters the skin surface.

8. An infusion set as claimed in claim 1, wherein said main hub is secured to the skin surface via an adhesive layer.

9. A method for targeting a desired depth to deliver content to an upper skin surface, comprising the steps of:
   enclosing a main hub and a needle hub in a slidable top cover;
   disposing a needle fixed to said needle hub at a first angle relative to said skin surface in a free state;
   securing said main hub on a skin surface, said main hub including an insertion track, wherein said needle deflects to an angle relative to said skin surface that is different from said first angle; and
   applying a motion to said needle to insert said needle into said skin surface, said needle returning toward the first angle relative to said skin surface; wherein
   a base of said needle pivots while traveling on said insertion track during said motion.

10. The method for targeting a desired depth of claim 9, further comprising:
   releasing the motion to said needle to place the needle at a third angle.

11. The method for targeting a desired depth of claim 10, wherein a difference between the first angle and the third angle is smaller than a difference between a second angle during said application of said motion and the third angle.

12. The method for targeting a desired depth of claim 11, wherein the motion is at an angle relative to the skin surface that is different from the first, second and third angles of the needle relative to the skin surface.

13. The method for targeting a desired depth of claim 10, wherein the first angle and the third angle relative to the skin surface are substantially similar.

14. The method for targeting a desired depth of claim 9, wherein the motion is substantially parallel to the skin surface.

15. The method for targeting a desired depth of claim 14, wherein the motion is applied by a user in the direction of the insertion track when the needle enters the skin surface.

16. The method for targeting a desired depth of claim 9, wherein the main hub is secured to the skin surface via an adhesive layer.

* * * * *